United States Patent
Yamazaki et al.

(10) Patent No.: US 6,518,410 B2
(45) Date of Patent: Feb. 11, 2003

(54) SULFOQUINOVOSYLACYLGLYCEROL DERIVATIVE, AND USE THEREOF AS MEDICAMENTS

(75) Inventors: Takayuki Yamazaki, Noda (JP); Fumio Sugawara, Niiza (JP); Keisuke Ohta, Noda (JP); Kazuyoshi Masaki, Sakado (JP); Kotaro Nakayama, Yotsukaido (JP); Kengo Sakaguchi, Tsukuba (JP); Noriyuki Sato, Sapporo (JP); Hiroeki Sahara, Sapporo (JP); Tatsuya Fujita, Sapporo (JP)

(73) Assignee: Toyo Suisan Kaisha, Ltd., Tokyo (JP)

( * ) Notice: Subject to any disclaimer, the term of this patent is extended or adjusted under 35 U.S.C. 154(b) by 0 days.

(21) Appl. No.: 09/949,907

(22) Filed: Sep. 10, 2001

(65) Prior Publication Data

US 2002/0052327 A1 May 2, 2002

Related U.S. Application Data

(63) Continuation-in-part of application No. 09/258,617, filed on Feb. 26, 1999, now abandoned, and a continuation-in-part of application No. PCT/JP00/01231, filed on Mar. 2, 2000.

(30) Foreign Application Priority Data

Mar. 11, 1999 (JP) .......................... 11-065208
Jun. 23, 1999 (JP) .......................... 11-176881

(51) Int. Cl.[7] .......................... A61K 31/70; C07H 5/10
(52) U.S. Cl. .......................... 536/4.1; 536/54; 536/118; 514/25
(58) Field of Search .......................... 536/4.1, 54, 118; 514/25

(56) References Cited

U.S. PATENT DOCUMENTS

| | | | |
|---|---|---|---|
| 5,489,578 A | 2/1996 | Rosen et al. | 514/61 |
| 5,695,752 A | 12/1997 | Rosen et al. | 424/94.61 |
| 5,783,693 A | 7/1998 | Bertozzi et al. | 536/124 |
| 6,395,886 B1 | 5/2002 | Yamazaki et al. | 536/4.1 |
| 6,444,795 B1 | 9/2002 | Yamazaki et al. | 536/4.1 |

FOREIGN PATENT DOCUMENTS

| | | |
|---|---|---|
| JP | 5130996 | 10/1980 |
| JP | 3052815 | 3/1991 |
| JP | 3052816 | 3/1991 |
| JP | 3066603 | 3/1991 |
| JP | 0040159 | 9/1991 |
| JP | 3246203 | 11/1991 |
| JP | 7-149786 | 6/1995 |
| JP | 7-242691 | 9/1995 |
| JP | 1106395 | 4/1999 |
| JP | 2000-143516 A | 5/2000 |
| WO | WO 91/02521 | 3/1991 |
| WO | WO 97/40838 | 11/1997 |

OTHER PUBLICATIONS

U.S. patent application Ser. No. 09/934,874, Yamazaki et al.
U.S. patent application Ser. No. 09/939,338, Yamazaki et al, filed Feb. 21, 2002.
U.S. patent application Ser. No. 09/939,153, Yamazaki et al.
S. Kashima et al., "A Study of Polymerase Inhibitors of Higher Plants, Nippon Nogeikagaku Kaishi", vol. 72, Mar. 5, 1998, p. 82, Abstr. No. 2A12P22.
Peer et al., "Synthesis of an L–Fucose–Derived Cyclic Nitrone and its Conversion to +–L–Fucosidase Inhibitors," Helvetica Chemica Acta, 82(7), 1044–1065 (Jul. 7, 1999).
Sanders et al., "Synthesis of Sulfated Trisaccharide Ligands for the Selectins," Tetrahedron, 53(48), 16391–16422 (Dec. 1, 1997).
Arasappan et al., "Regiospecific 4, 6–Functionalization of Pyranosides via Dimethylboron Bromide–Mediated Cleavage of Phthalide Orthoesters," J.American Chemical Society, 117(1), 177–183 (Jan. 11, 1995).
Thiem et al., "Synthesen von Methyl–4–O–(β–D–curaocsyl)–α–D–curamicosid, dem Glycosid der Disaccharideinheit E–F von Flambamycin und Isomeren," Justus Liebig's Annalen der Chemie, 1987(4), 289–295 (Apr. 1987).

(List continued on next page.)

Primary Examiner—Johann Richter
Assistant Examiner—L E Crane
(74) Attorney, Agent, or Firm—Frishauf, Holtz, Goodman & Chick, P.C.

(57) ABSTRACT

A method for immunosuppression in a subject comprising administering to the subject in need thereof, a pharmaceutically effective amount of at least one sulfoquinovosylacylglycerol derivative represented by General formula (1-1):

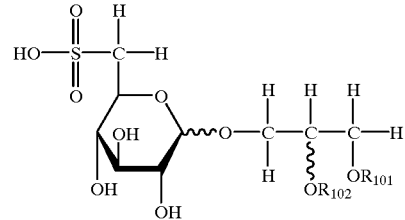

(1-1)

wherein $R_{101}$ represents an acyl residue of a higher fatty acid, and $R_{102}$ represents a hydrogen atom or an acyl residue of a higher fatty acid; and a pharmaceutically acceptable salt thereof. Of the sulfoquinovosylacylglycerol derivatives, β-sulfoquinovosylacylglycerols are novel compounds. The present invention also relates to pharmaceutical composition comprising a pharmaceutically effective amount of the β-sulfoquinovosylacylglycerols and/or its pharmaceutically acceptable salt; and a pharmaceutically acceptable excipient. The pharmaceutical composition may be used as an immunosuppressive agent, anticancer agent and DNA polymerase α inhibitor.

29 Claims, 4 Drawing Sheets

OTHER PUBLICATIONS

Fujimaki et al., "Conversion of 1,6–Anhydromaltose into Pseudodisaccharides Containing Aminocyclitols as Constituent," *Agricultural & Biological Chemistry*, 44(9), 2055–2059 (Sep., 1980).

Tulloch et al., "Combination and Positional Distribution of Fatty Acids in Plant Sulfolipids," *Hoppe–Seyler's Zeitschrift Physiol. Chem.*, 354, 879–889 (Aug., 1973).

Fusetani et al., "Structures of Two Water Soluble Hemolysins Isolated from the Green Alga *Ulva pertusa*," *Agricultural and Biological Chemistry*, 39(10), 2021–2025 (Oct., 1975).

Kitagawa et al., "Sulfoglycolipid from the Sea Urchin *Anthocidaris vrassisspina* A. Agassiz," *Chemical & Pharmaceutical Bulletin*, 27(8), 1934–1937 (Aug., 1979).

Gustafson et al., "AIDS–Antiviral Sulfolipids From Cyanobacteria (Blue–Green Algae)," *Journal of the National Cancer Institute(USA)*, 81(16), 1255–1258 (Aug. 16, 1989).

Adebodun et al., "Spectroscopic Studies of Lipids and Biological Membranes: Carbon–13 and Proton Magic-Angle Sample–Spinning Nuclear Magnetic Resonance Study of Glycolipid–Water Systems," *Biochemistry*, 31(18), 4502–4509 (May, 1992).

Gage et al., "Comparison of Sulfoquinovosyl Diacylglycerol from Spinach and the Purple Bacterium *Rhodobacter sphaeroides* by Fast Atom Bombardment Tandem Mass Spectrometry," *Lipids*, 27(8), 632–636 (Aug., 1992).

Morimoto et al., Studies on Glycolipids. VII. Isolation of Two New Sulfoquinovosyl Diacylglycerols from the Green Alga *Chlorella vulagris*, *Chemical & Pharmaceutical Bulletin*, 41(9), 1545–1548 (Sept., 1993).

Amarquaye et al., "A New Glycolipid from *Byrsonima crassifolia*," *Planta Medica*, 60(1), 85–86 (Feb., 1994).

Murakami et al., "Enzymatic Transformation of Glyceroglycolipids into *sn*–1 and *sn*–2 Lysoglyceroglycolipids by Use of *Rhizopus arrhizus* Lipase," *Tetrahedron*, 50(7), 1993–2002 (Feb. 14, 1994).

Vishwanath et al., "Interaction of Plant Lipids with 14 kDa Phospholipase $A_2$ Enzymes," *Biochemical Journal*, 320(1), 93–99 (Nov. 15, 1996).

Golik et al., "Isolation and Structure Determination of Sulfonoquinovosyl Dipalmitoyl Glyceride, a P–Selectin Receptor Inhibitor from the Alga *Dictyochloris Fragrans*," *Journal of Natural Products*, 60(4), 387–389 (Apr., 1997).

Vasänge et al., "A Sulfonoglycopilids from the Fern *Polypodium decumanum* and its Effect on the Platelet Activating–factor Receptor in Human Neutrophils," *Journal of Pharmaceutical Pharmacology*, 49(5), 562–566 (May, 1997).

Kim et al., "Structural Identification of Glycerolipid Molecular Species Isolated from Cyanobacterium *Synechocytis* sp. PCC 6803 Using Fast Atom Bombardment Tandem Mass Spectrometry," *Analytical Biochemistry*, 267, 260–270 (1999).

Yoshiyuki Mizushina, Shonen Yoshida, Akio Matsukage and Kengo Sakaguchi, "The Inhibiting Action of Fatty Acids on DNA Polymerase $\beta$", *Biochemica et Biophysica Acta*, 1336, (1997), 509–521.

Keisuke Ohta et al., "Sulfoquinovosyldiacylglycerol, KM043, a New Potent Inhibitor of Eukaryctic DNA Polymerases and HIV–Reverse Transcriptase Type 1 from a Marine Red Alga, *Gigartina tenella*", *Chem. Pharm. Bull.*, 46(4), 684–696 (1998).

Yoshiyuki Mizushina et al., "Studies on Inhibitors of Mammalian DNA Polymerase $\alpha$ and $\beta$", *Biochemical Pharmacology*, 55, 537–541 (1998).

H. Sahra et al., "In vivo anti–tumour effect of 3'–sulphonoquinovosyl 1'–monoacylglyceride isolated from sea urchin (*Strongylocentrotus intermedius*) intestine", *British Journal of Cancer*, 75(3), 324–332 (1997).

Dan M. Gordon et al., "Synthesis of a Cyanobacterial Sulfolipid: Confirmation if Its Structure, Stereochemistry, and Anti–HIV–1 Activity", *J. Amer. Chem. Soc.*, 114, 659–663 (1992).

Roy Gigg et al., "Synthesis of 3–O–(6–Deoxy–6–sulpho–α–D–glucopyranosyl)–1, 2–di–O–hexadecanoyl–L–glycerol, Sulphoquinovosyl Diglyceride", *Journal of the Chemical Society Perkin Transaction I*, 2490–2493 (1980).

Hideaki Shirahashi et al., "Isolation and Identification of Anti–tumor–Promoting Principles from the Fresh–Water Cyanobacterium *Phormidium tenue*", *Chem. Pharm. Bull.*, 41(9), 1664–1666 (1993).

*Pharm Quang Lien et al., "Structures, teneurs et compositions des esters sulfuriques, sulfoniques, phosphoriques des glycosyldiglcerides de trois fucasees", *Biochimie*, 58, 1367–1380 (1976).

Michael Keusgen et al., "Sulfoquinovosyl Diacylglycerols from the Alga *Heterosigma carterae*", *Lipids*, 1101–1112, 32, (1997).

Byeng Wha Son, "Glycolipids from *Gracilaria Verrucosa*", *Pyhtochemistry*, 29, 307–309 (1990).

Luca Rastrelli, "Glycolipids from Byrsonima Crassifolia", *Phytochemistry*, 45, 647–650 (1997).

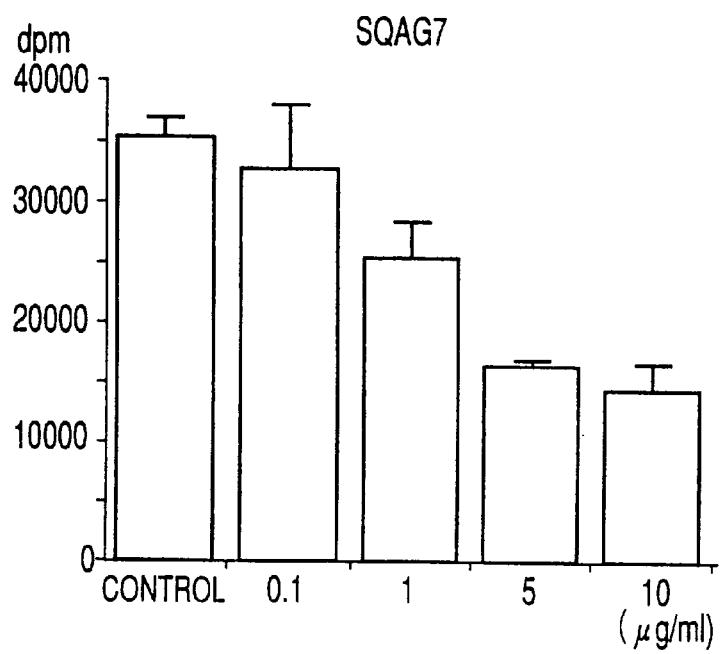
F I G. 3
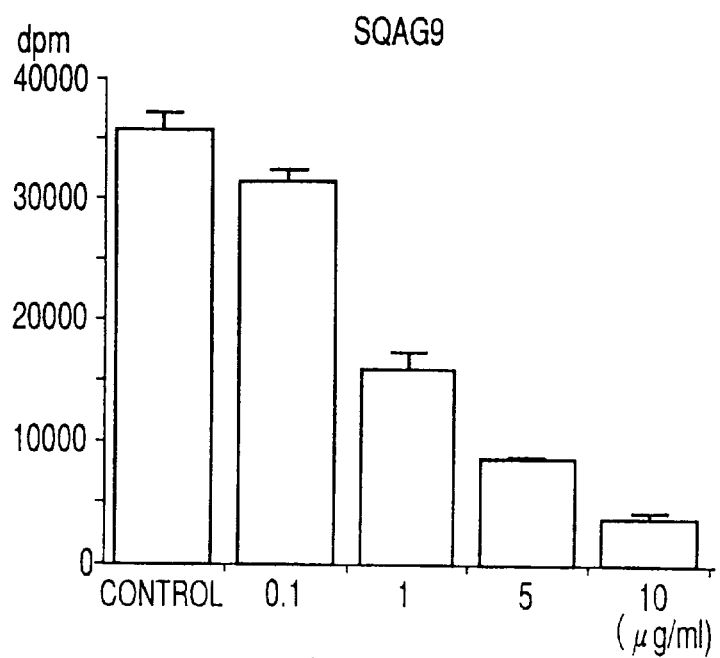
F I G. 4

SULFOQUINOVOSYLACYLGLYCEROL DERIVATIVE, AND USE THEREOF AS MEDICAMENTS

CROSS-REFERENCE TO RELATED APPLICATIONS

This is a Continuation-in-Part Application of U.S. patent application No. 09/258,617, filed Feb. 26, 1999, now abandoned, and PCT Application No. PCT/JP00/01231, filed Mar. 2, 2000, which was not published under PCT Article 21(2) in English.

This application is based upon and claims the benefit of priority from the prior Japanese Patent Application No. 11-065208, filed March 11, 1999, and 11-176881, filed Jun. 23, 1999.

BACKGROUND OF THE INVENTION

1. Field of the Invention

The present invention relates to a novel immunosuppressive agent. More specifically, the present invention relates to a novel immunosuppressive agent containing, as an effective ingredient, a certain α/β-sulfoquinovosylacylglycerol derivative and/or a salt thereof.

The present invention also relates to an anticancer agent, and in particular to an anticancer agent comprising, as an effective ingredient, a certain β-sulfoquinovosylacylglycerol derivative and/or a salt thereof.

Further, the present invention also relates to a DNA polymerase α inhibitor comprising, as an effective ingredient, a certain β-sulfoquinovosylacylglycerol derivative and/or a salt thereof.

The β-sulfoquinovosylacylglycerol derivatives that are the effective ingredients of the anticancer agent, immunosuppressive agent and DNA polymerase α inhibitor of the present invention, are novel compounds. The present invention also relates to the novel β-sulfoquinovosylacylglycerol derivatives.

2. Description of the Related Art

In clinical treatment presently performed, transplantation can be employed to treat chemotherapeutically untreatable diseases. Transplantation is the technology for treating a disease by replacing partly or entirely of a diseased organ with a healthy organ taken from another individual. Organ transplantation has been performed with respect to a wide variety of organs such as kidney, liver, lung, intestine, heart, pancreas, and cornea. The number of organ transplantations has been increased.

The immune response of skin is inherently high. However, skin transplantation can be made successfully if a graft skin transplanted from one person to another can be kept alive for at least a few weeks. This is because new dermal tissue, if a graft epidermis is kept alive for a few weeks, can regenerate itself, thereby recovering from a dermal tissue damage. Therefore, it is possible to make physical recuperation of serious and extensive burn or laceration by transplanting a dermal tissue from another person.

The most fearful problem residing in tissue or organ transplantation is a rejection caused by a recipient's immune response.

Under these circumstances, in order to develop an immunosuppressive agent capable of preventing the rejection in a recipient, thereby attaining permanent fixation of a transplanted organ, intensive studies have been conducted since the 1970s, particularly in European countries and U.S.A.

On the other hand, an immunosuppressive agent may also be important in treating autoimmune diseases such as rheumatism and collagen disease, since it can mitigate the symptoms to a certain degree.

Up to the present, cyclosporin A and FK506, etc., have been developed as immunosuppressive agents. However, the functional mechanisms of these immunosuppressive agents resemble each other and their chronic toxicity is a matter of concern. Thus, to attain prolonged life in next-generation organ transplantation, another type of immunosuppressive agent is desired which has a lower toxicity based on a different chemical structure, and thus, different functional mechanism can be expected.

It has been found that naturally-occurring sulfur-containing glycolipids have pharmaceutical activities such as an anticancer effect (Sahara et al., British Journal of Cancer, 75(3), 324–332, (1997)); inhibitory activities against DNA polymerase (Mizushina et al., Biochemical Pharmacology, 55, 537–541 (1998), Ohta et al., Chemical & Pharmaceutical Bulletin, 46(4), 1998)); and HIV suppressive effect (National Patent Publication No. 5-501105). However, it has not yet been found that a sulfur-containing glycolipid, in particular, a sulfoquinovosylacylglycerol derivative, has an immunosuppressive activity.

Further, almost all of the sulfoquinovosylacylglycerol derivatives described in the documents are derived from natural products. Thus, the bonding between the sugar moiety and the glycerol moiety is an α-configuration. A β-sulfoquinovosylacylglycerol in which the bonding between the sugar moiety and the glycerol moiety is a β-configuration, has not yet been known.

BRIEF SUMMARY OF THE INVENTION

An object of the present invention is to provide a novel immunosuppressive agent. More specifically, the object of the present invention is to provide an immunosuppressive agent showing low toxicity and usability of long-term administration, and high immunosuppressive activity as well.

Other objects of the present invention is to provide a novel anticancer agent and DNA polymerase α inhibitor.

The present inventors have conducted studies to attain the aforementioned object. As a result, they found that specific sulfoquinovosylacylglycerol derivatives have a remarkable immunosuppressive activity and accomplished the present invention. The present invention provides an immunosuppressive agent containing, as an active ingredient, at least one compound selected from the group consisting of:

compounds represented by Formula (1-1):

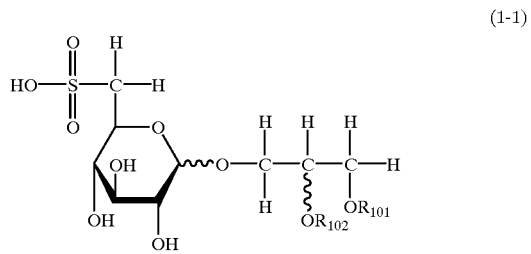

(1-1)

where $R_{101}$ represents an acyl residue of a higher fatty acid, and $R_{102}$ represents a hydrogen atom or an acyl residue of a higher fatty acid, and a pharmaceutically acceptable salt thereof.

The present invention also provides an anticancer agents and DNA polymerase α inhibitor containing, as an active ingredient, at least one compound selected from the group consisting of:

compounds represented by Formula (1-2):

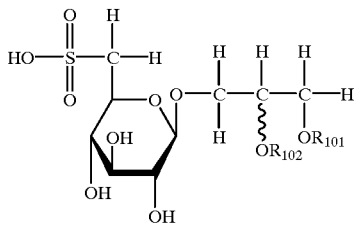

(1-2)

where $R_{101}$ and $R_{102}$ have the same meaning as $R_{101}$ and $R_{102}$ in General formula (1-1), respectively, and a pharmaceutically acceptable salt thereof.

The β-sulfoquinovosylacylglycerol derivatives represented by General formula (1-2) mentioned above are novel compounds. The present invention also provides the β-sulfoquinovosylacylglycerol derivatives represented by General formula (1-2).

Additional objects and advantages of the present invention will be set forth in the description which follows, and in part will be obvious from the description, or may be learned by practice of the present invention. The objects and advantages of the present invention may be realized and obtained by means of the instrumentalities and combinations particularly pointed out hereinafter.

BRIEF DESCRIPTION OF THE SEVERAL VIEWS OF THE DRAWING

FIG. 3 shows the relationship between the concentration of the compound (SQAG 7) represented by Formula (1-1) and the immunosuppressive activity; and FIG. 4 shows the relationship between the concentration of the compound (SQAG 9) represented by Formula (1-1) and the immunosuppressive activity.

DETAILED DESCRIPTION OF THE INVENTION

Figure 1:
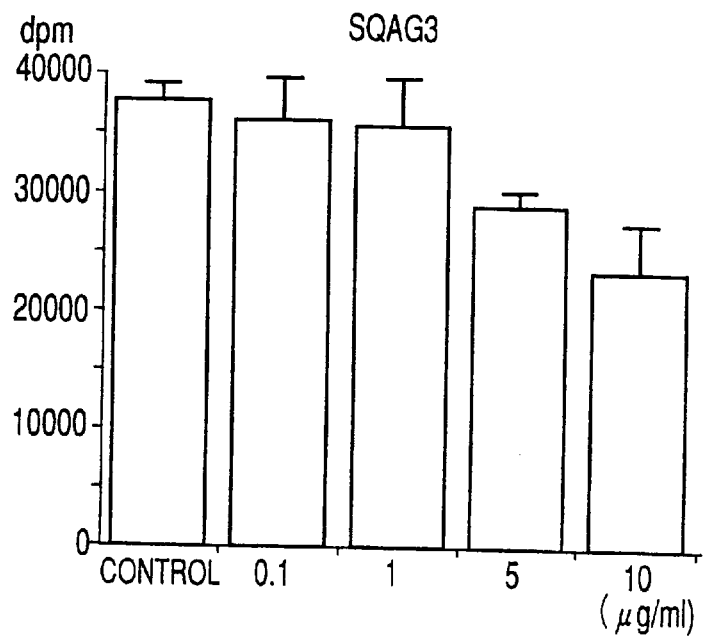
FIG. 1 shows the relationship between the concentration of the compound (SQAG 3) represented by Formula (1-1) and the immunosuppressive activity.
Figure 2:
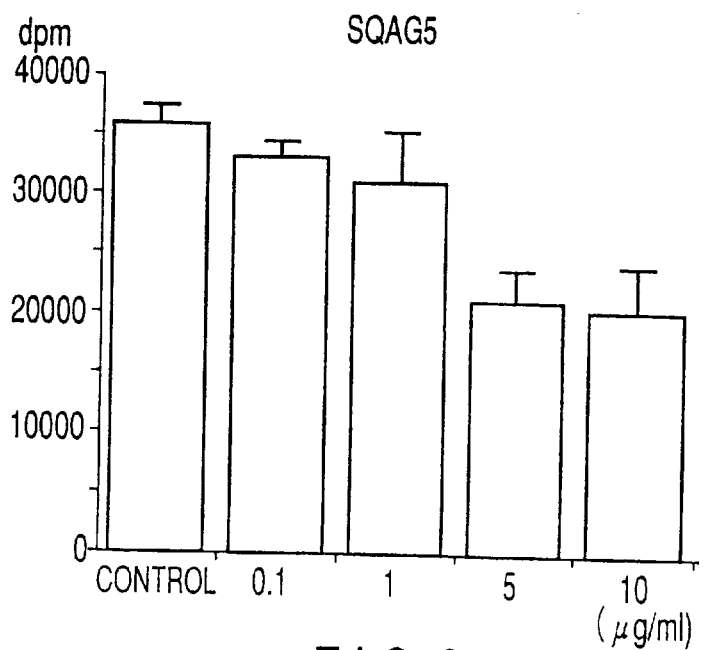
FIG. 2 shows the relationship between the concentration of the compound (SQAG 5) represented by Formula (1-1) and the immunosuppressive activity.

In the specification, the term "carbon atoms" of a protecting group refers to the number of carbon atoms assuming that the protecting group is unsubstituted. To be more specific, when the group represented by $R^6$ is a substituted alkyl group, its number of carbon atoms is that of the alkyl group itself, and the number of carbon atoms of the substituent on the alkyl group is not counted. The same conditions are applicable to the case where the protecting group is other than the alkyl group.

In the first place, we will more specifically explain the active ingredient contained in the immunosuppressive agent of the present invention, that is, a sulfoquinovosylacylglycerol derivative represented by Formula (1-1):

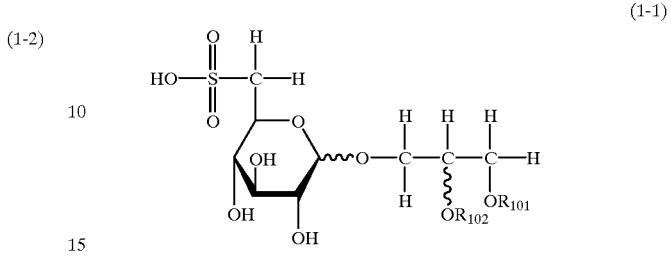

(1-1)

where $R_{101}$ represents an acyl residue of a higher fatty acid, and $R_{102}$ represents a hydrogen atom or an acyl residue of a higher fatty acid.

In Formula (1-1), $R_{101}$ represents an acyl residue of a higher fatty acid. Fatty acids giving the acyl residue represented by $R_{101}$ include straight-chain or branched-chain, saturated or unsaturated higher fatty acids.

The acyl residues of straight-chain or branched-chain higher fatty acids represented by $R_{101}$ include groups represented by R—C(=O), where R represents an alkyl or alkenyl group having 13 or more carbon atoms. The number of carbon atoms of the alkyl and alkenyl groups represented by R of R—C(=O) is preferably 13 or more and 25 or less, and more preferably, an odd number within 15–25. This is because if the number of carbon atoms of R exceeds 25, the manufacturing cost increases. When R is an alkenyl grop, the position of the double bond contained therein is not particularly limited. Examples of the alkenyl group are the alkenyl groups of commercially available fatty acids, such as those described, for example, on pages 67 to 75 in a catalogue of "KENKYUYOU SHIYAKU; TEN-NENBUTSU, SHISHITSU, TOUSHITSU (AGENTS FOR RESEARCH; NATURAL PRODUCTS, LIPIDS, CARBOHYDRATES)", distributed by FUNAKOSHI KABUSHIKIKAISYA, Japan, March, 1999), the discloser of which is enclosed herein by reference. In Formula (1-1), $R_{102}$ represents a hydrogen atom or an acyl residue of a higher fatty acid. The acyl residues represented by $R_{102}$ have the same meaning as those of $R_{101}$ mentioned above.

When both $R_{101}$ and $R_{102}$ are acyl residues of a higher fatty acid(s), these may be the same or different. However, they are preferably the same in view of manufacturing facility.

The sugar skeleton of sulfoquinovoside in Formula (1-1) may take either a boat or chair conformation. However, the chair conformation is preferable in view of stability. The absolute configuration of the carbon (asymmetric carbon) at the 2-position of the glycerol moiety may be either the S- or R-configuration.

The bonding between sulfoquinovoside and glycerol is either an α- or β-bonding. However, the present inventors have found that, in the immunosuppressive activity assay using cultured cells, the β-anomers represented by General formula (1-2) have remarkably higher immunosuppressive activities than the α-anomers, which was unexpected.

The β-sulfoquinovosylacylglycerol derivatives represented by General formula (1-2):

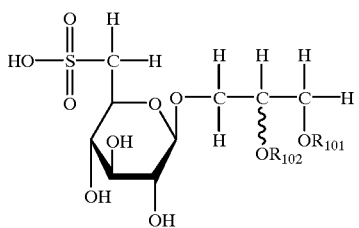

(1-2)

where $R_{101}$ and $R_{102}$ have the same meaning as $R_{101}$ and $R_{102}$ of General formula (1-1), respectively, will be explained in detail.

The acyl residues represented by $R_{101}$ of General formula (1-2) have the same meaning as $R_{101}$ of General formula (1-1), and preferable carbon atoms thereof are also the same as those of General formula (1-1). Similarly, the acyl residues represented by $R_{102}$ of General formula (1-2) have the same meaning as $R_{102}$ of General formula (1-1), and preferable carbon atoms thereof are also the same as those of General formula (1-1).

The sugar skeleton of sulfoquinovoside in Formula (1-2) and the absolute configuration of the carbon (asymmetric carbon) at the 2-position of the glycerol moiety are the same as those mentioned for Formula (1-1).

From the viewpoint of particularly an anticancer effect against colon cancer or gastric cancer, $R_{102}$ is preferably a hydrogen atom.

Specific compounds represented by General formula (1-1) are set forth in Table 1 below, however, the present invention is not limited to these.

TABLE 1

(1-1)

| Compound | $R_{101}$— | $R_{102}$— | Bond between the C-1 of the glucose and the glyceride |
|---|---|---|---|
| SQAG 1 | $CH_3(CH_2)_{12}CO$— | $CH_3(CH_2)_{12}CO$— | α |
| SQAG 2 | $CH_3(CH_2)_{12}CO$— | H | α |
| SQAG 3 | $CH_3(CH_2)_{14}CO$— | $CH_3(CH_2)_{14}CO$— | α |
| SQAG 4 | $CH_3(CH_2)_{14}CO$— | H | α |
| SQAG 5 | $CH_3(CH_2)_{16}CO$— | $CH_3(CH_2)_{16}CO$— | α |
| SQAG 6 | $CH_3(CH_2)_{16}CO$— | H | α |
| SQAG 7 | $CH_3(CH_2)_{14}CO$— | $CH_3(CH_2)_{14}CO$— | β |
| SQAG 8 | $CH_3(CH_2)_{14}CO$— | H | β |
| SQAG 9 | $CH_3(CH_2)_{16}CO$— | $CH_3(CH_2)_{16}CO$— | β |
| SQAG 10 | $CH_3(CH_2)_{16}CO$— | H | β |
| SQAG 11 | $CH_3(CH_2)_{18}CO$— | H | α |
| SQAG 12 | $CH_3(CH_2)_{20}CO$— | H | α |
| SQAG 13 | $CH_3(CH_2)_{22}CO$— | H | α |
| SQAG 14 | $CH_3(CH_2)_{24}CO$— | H | α |

The sulfoquinovosylacylglycerol derivatives of the present invention can be prepared via (Step A) to (Step J) in accordance with the following reaction procedure.

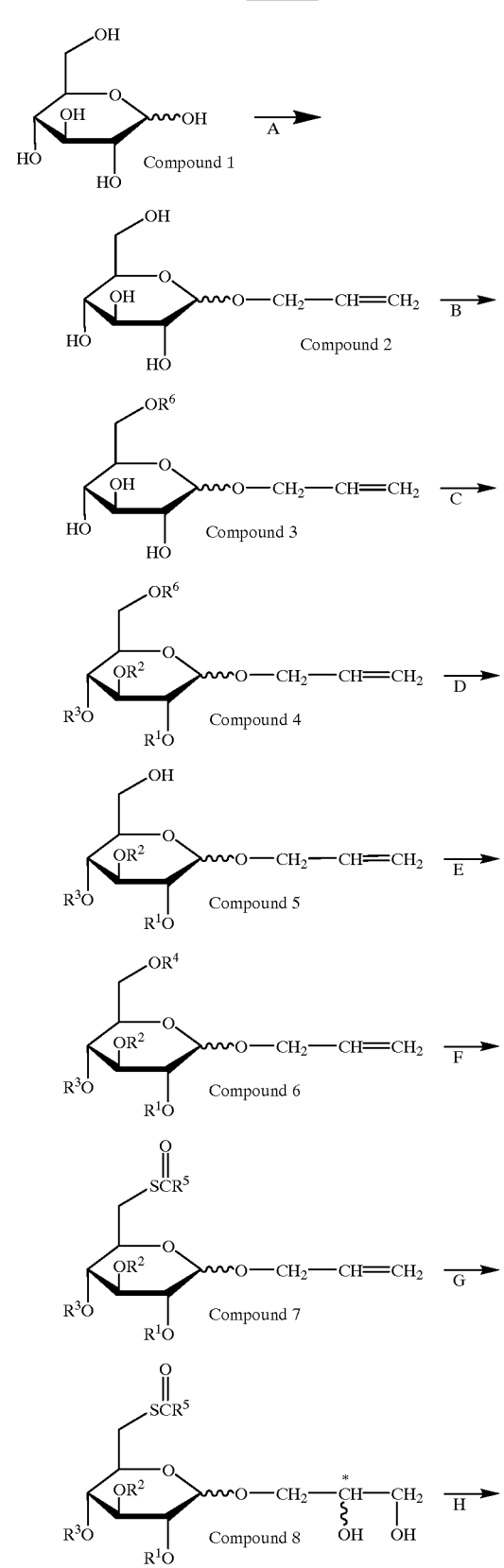

Scheme 1

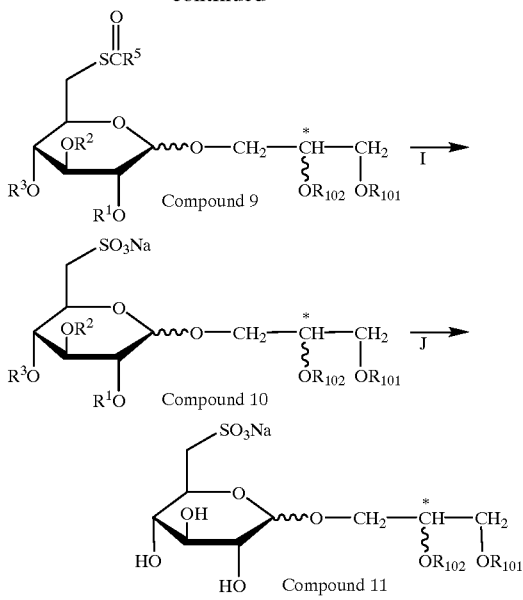

Compound 9

Compound 10

Compound 11

(Step A) The hydroxyl group bonded to the C1 carbon of D-glucose is converted into a 2-propenyl group. (Step B) The hydroxyl group of the C6 carbon of the glucose is protected. (Step C) The hydroxyl groups bonded to the C2, C3 and C4 carbons of the glucose are protected. (Step D) The protecting group of the C6 carbon previously protected is deprotected. (Step E) The hydroxyl group bonded to the C6 carbon is substituted with a group (for example, an alkylsulfonyloxy group or arylsulfonyloxy group) which can be converted to a carbonylthio group. (Step F) The C6 carbon is converted into a carbonylthio group. (Step G) The 2-propenyl group bonded to the C1 carbon is converted into a diol. (Step H) Each of the hydroxyl groups of the diol thus obtained is esterified with a desired higher fatty acid. (Step I) The carbonylthio group at the C6 carbon is converted into a sulfonate salt. (Step J) The protecting groups of C2, C3 and C4 carbons of the sulfonate salt obtained are deprotected. As a result, a salt of a sulfoquinovosylacylglycerol derivative of the present invention can be produced. The salt thus obtained is subjected to titration with an acid such as hydrochloric acid to give the sulfoquinovosylacylglycerol derivative of the present invention.

The aforementioned Steps A–J will be further explained in detail.

In Step A, the 2-propenylation is carried out by reacting the glucose with allyl alcohol in the presence of a strong acid, such as trifluoromethanesulfonic acid, usually at room temperature to 100° C., preferably from 80 to 90° C., for a half day to two days. However, the reaction time varies depending upon the reaction conditions.

In Step B, the hydroxyl group bonded to the C6 carbon is protected to obtain the compound to which —$OR^6$ is bonded at the C6 carbon (where $R^6$ represents an alkyl or substituted silyl group).

As the compound capable of protecting the hydroxyl group, a compound can be used which can provide an alkyl or substituted silyl group as the $R^6$ group.

Examples of the alkyl group represented by $R^6$ preferably include bulky and substituted lower alkyl groups. The substituents of the bulky and substituted alkyl groups include methyl and phenyl groups. The specific examples of the substituted alkyl group include t-butyl and trityl groups.

When the group represented by $R^6$ represents a substituted silyl group, examples of substituents of the substituted silyl group include lower alkyl groups, preferably alkyl groups having 1–4 carbon atoms (for example, methyl, ethyl, isopropyl and t-butyl groups); and aryl groups, preferably aryl groups having 6 carbon atoms (for example, a phenyl group). The substituted silyl group represented by $R^6$ preferably includes tri-substituted silyl groups, more preferably, a t-butyldiphenylsilyl group.

When the compound 3, where $R^6$ represents an alkyl group, is to be obtained, the protection of the hydroxyl group in Step B can be carried out by adding a compound represented by $R^6$—X (where $R^6$ represents the alkyl group defined above, and X represents a halogen atom such as chlorine atom) to a solution of the compound 2 dissolved in an organic solvent, such as anhydrous pyridine, and reacting the solution mixture at room temperature in the presence of a catalyst such as p-dimethylaminopyridine (DMAP). As the compound $R^6$—X, trityl chloride is preferably used in view of manufacturing cost and reaction facility.

When the compound 3, where $R^6$ represents a substituted silyl group, is to be obtained, t-butyldiphenylsilyl chloride, for example, is used as the compound $R^6$—X, and the reaction is carried out in the presence of a catalyst, such as imidazole, at room temperature for a half day to two days. Note that the reaction time varies depending upon the reaction conditions.

In Step C, the hydroxyl groups bonded to the C2, C3 and C4 carbons are protected and converted into —$OR^1$, —$OR^2$ and —$OR^3$, respectively, where $R^1$ to $R^3$ independently represent an alkyl or substituted silyl group. The protection of these hydroxyl groups can be carried out by activating, with sodium hydride, the hydroxyl groups bonded to the C2, C3 and C4 carbons of the compound 3 dissolved in an organic solvent, such as N, N-dimethylformamide (DMF), and reacting with the compound capable of protecting these hydroxyl groups at room temperature.

As the compound capable of protecting the hydroxyl groups, benzyl bromide, p-methoxybenzyl bromide, t-butyldimethylsilyl chloride or triethylsilyl chloride may be used. The reaction using the compound capable of protecting the hydroxyl groups can be carried out under a suitable reaction condition for each of the protecting groups.

The deprotection of the protecting group bonded to the C6 carbon in Step D may be carried out by reacting a solution of the compound 4 dissolved in an organic solvent, such as methanol, in the presence of a catalyst, such as p-toluenesulfonic acid, for a half day to one day at room temperature. The reaction time varies depending upon the reaction conditions.

In Step E, $R^4$, that is, an alkylsulfonyl or arylsulfonyl group is bonded to the hydroxyl group at the C6 carbon of the compound 5, so that the hydroxyl group is converted into —$OR^4$ to give the compound 6.

The reaction to give the —$OR^4$ group is performed by adding a compound having the alkylsulfonyl group or a compound having the arylsulfonyl group to a solution of the compound 5 dissolved in an organic solvent, and reacting them. The alkyl groups of the compound having the alkylsulfonyl group preferably include unsubstituted alkyl groups, more preferably, lower alkyl groups, much more preferably, alkyl groups having 1–2 carbon atoms (methyl and ethyl groups). The compound having an alkylsulfonyl group can be represented by $R^{4'}$—X, where $R^{4'}$ represents an alkylsulfonyl group, and X represents a halogen atom. Specific examples include methanesulfonyl chloride and ethanesulfonyl chloride.

On the other hand, the aryl group of the compound having the arylsulfonyl group may include unsubstituted and substituted aryl groups, preferably aryl groups having 6 carbon atoms (e.g., a phenyl group). In the case of the substituted aryl group, examples of the substituent thereof include p-methyl and p-methoxy groups. Examples of the compound having an arylsulfonyl group include compounds represented by $R^{4''}$—X, where $R^{4''}$ represents an arylsulfonyl group, and X represents a halogen atom. Specific examples include p-toluenesulfonyl chloride, p-methoxybenzenesulfonyl chloride and benzenesulfonyl chloride.

Of the compounds having an alkylsulfonyl or arylsulfonyl group, a compound having a tosyl group is preferably used from the viewpoint of reaction facility.

In the reaction of Step E, as an organic solvent, for example, pyridine or dichloromethane may be used.

The reaction mentioned above may be performed, as the case may be, in the presence of a catalyst, such as DMAP, at room temperature for 2 hours to one day. The reaction time varies depending upon the reaction conditions.

In Step F, the sulfonyloxy group (—$OR^4$) of the compound 6 is replaced with a carbonylthio group represented by —SC(=O)$R^5$, where $R^5$ represents a hydrogen atom, an alkyl or aryl group.

In the reaction, a compound capable of substituting the alkylsulfonyloxy or arylsulfonyloxy group of the compound 6 with the carbonylthio group, is allowed to react in an organic solvent to give a compound 7. Hereinafter, this compound will be referred to as "O-substituted →S-substituted compound". Examples of the O-substituted →S-substituted compound include alkali metal salts and alkali earth metal salts of a thiocarboxylic acid. Examples of the thiocarboxylic acid include thioformic acid, lower thiocarboxylic acids, preferably aliphatic thiocarboxylic acids each having 1–5 carbon atoms in its aliphatic hydrocarbon moiety (for example, thioacetic acid or thiopropionic acid), and aromatic thiocarboxylic acids each having 6–10 carbon atoms in its aromatic hydrocarbon moiety (for example, thiobenzoic acid).

The alkali metal that forms a salt with the thiocarboxylic acid includes potassium and sodium. The alkali earth metal includes magnesium and calcium.

Of the above-mentioned O-substituted →S-substituted compounds, salts of thioacetic acid may be preferably used since a reaction can proceed stably and the sulfur atom can be easily oxidized in a later step.

Examples of an organic solvent used in the reaction include alcohol, for example, methanol, ethanol and propanol, N,N-dimethylformamide and dimethylsulfoxide.

The aforementioned reaction may be performed usually at room temperature to the boiling point of a solvent to be used while stirring for one hour to one day. Note that the reaction time varies depending upon the reaction conditions.

The dihydroxylation of Step G may be performed by adding an oxidizing agent, such as osmium tetraoxide, to a solution of the compound 7 dissolved in a solvent mixture, such as a mixture of t-butanol and water, and then reacting the resultant mixture in the presence of a re-oxidizing agent, such as trimethylamine N-oxide, at room temperature for one hour to three days. Note that the reaction time varies depending upon the reaction conditions.

By the esterification of Step H, a sulfoquinovosylacylglycerol derivative having desired higher fatty acids each bonded, through an ester-bond, to its glycerol moiety can be obtained.

This reaction can be carried out by adding a higher fatty acid corresponding to a final product to a solution of the compound 8 dissolved in a suitable organic solvent, such as dichloromethane, and then reacting the resultant mixture, if necessary, in the presence of a suitable catalyst, such as ethyldimethylaminopropylcarbodiimide (EDCI)-DMAP.

In the reaction of Step H, as the fatty acid to be added, use may be made of a higher fatty acid whose acyl group is that represented by $R_{101}$ of Formula (1-1), i.e., a straight-chain or branched-chain, saturated or unsaturated higher fatty acid.

In the reaction of Step H, the compound 9 is obtained in the form of a mixture of a diacylester and a monoacylester. The diacylester herein is represented by Formula (1-1) of the present invention where each of $R_{101}$ and $R_{102}$ is an acyl residue of the higher fatty acid added. The monoacylester herein has the acyl residue of the higher fatty acid added, as the $R_{101}$ only. Two or more higher fatty acids may be added, if desired, in the reaction of Step H. In this case, the resultant mixture contains diacylesters represented by Formula (1-1) where $R_{101}$ and $R_{102}$ are the same or different acyl residues, and monoesters having different acyl residues as $R_{101}$.

If necessary, the mixture of the monoesters and diesters can be isolated from each other by, for example, chromatography, and subjected to the next reaction Step I. Furthermore, production of the monoester is suppressed as much as possible by setting the addition amount of the fatty acid to 2–3 times larger than that of the compound 8, in terms of mole, thereby the diester can be preferentially obtained.

In Step I, the conversion into a sulfonate salt can be carried out by adding an oxidizing agent, for example, OXONE (2$KHSO_5$, $KHSO_4$ and $K_2SO_4$) into a solution of the compound 9 dissolved in an organic solvent, which is buffered with acetic acid and potassium acetate, and then allowing the resultant mixture to react at room temperature for a half day to two days. Note that the reaction time varies depending upon the reaction conditions.

The deprotection of the protecting groups bonded to carbons at the C2 to C4 carbons in Step J can be carried out by a method suitable for a protecting group to be used and an acyl residue of the bonded higher fatty acid. For example, when the protecting group is a benzyl group and each of $R_{101}$ and $R_{102}$ is an acyl residue of a saturated higher fatty acid, the deprotection can be conducted by reacting a solution of a compound 10 dissolved in an organic solvent, such as ethanol, in the presence of a catalyst, such as palladium-activated carbon, under a hydrogen gas atmosphere at room temperature. Furthermore, when at least one of the acyl residues of the higher fatty acids represented by $R_{101}$ and $R_{102}$ is an acyl residue of an unsaturated higher fatty acid, a deprotection method suitable for a protecting group used and capable of retaining the double bond of the unsaturated fatty acid may be employed. For example, when the protecting group is a silyl group, the deprotection can be conducted by use of an acid catalyst (e.g., trifluoroacetic acid).

Note that glucose of a starting material usually takes α- and β-anomer configurations in a solution. Therefore, the product in each step results in a mixture of α- and β-anomers. The mixture may be separated into α- and β-anomers by chromatography.

Prior to the step B, if a step of reacting the compound 2 with benzaldehyde is performed to form benzylidene, it is possible to selectively crystallize the α-anomer and thereby separate it. Furthermore, if halogen such as bromin is bonded to the C1 carbon before the 2-propenylation of Step A, the propenyl group can be introduced into a β-configuration in a later reaction. In this way, β-anomers can be selectively synthesized.

The immunosuppressive agent of the present invention contains at least one compound selected from the group consisting of sulfoquinovosylacylglycerol derivatives represented by Formula (1-1) of the present invention and pharmaceutically acceptable salts thereof, as an active ingredient. Examples of the pharmaceutically acceptable salts employed in the immunosuppressive agent of the present invention include, but not limited to, a salt of a monovalent cation such as a sodium or potassium ion. Hereinafter, the compounds of the group consisting of sulfoquinovosylacylglycerol derivatives and pharmaceutically acceptable salts thereof are sometimes referred to as "immunosuppressive substance of the present invention".

Examples of the sulfoquinovosylacylglycerol derivative contained in the immunosuppressive substance of the present invention as an active ingredient include an isomer in which quinovose is bonded to glycerol with an α- or β-configuration, and an isomer having an asymmetric carbon at the C2 carbon of the glycerol moiety. The immunosuppressive substance of the present invention may include these isomers alone or in combination of two or more types of isomers as long as they adversely affect the activity of the immunosuppressive substance.

The immunosuppressive substance of the present invention can be orally or parenterally administered. Immunosuppressive substance of the present invention can be combined with, for example, a pharmaceutically acceptable excipient or diluent depending on an administration route thereby to form a medicinal formulation.

The forms of the agent suitable for oral administration include, solid-, semi-solid, liquid- and gas-states. Specific examples include, but not limited to, tablet, capsule, powder, granule, solution, suspension, syrup and elixir agents.

In order to formulate the immunosuppressive substance of the present invention into tablets, capsules, powders, granules, solutions or suspensions, the substance is mixed with a binder, a disintegrating agent and/or a lubricant, and, if necessary, the resultant is mixed with a diluent, a buffer, a wetting agent, a preservative and/or a flavor, by a known method. Examples of the binder include crystalline cellulose, cellulose derivatives, cornstarch and gelatin. Examples of the disintegrating agent include cornstarch, potato starch and sodium carboxymethylcellulose. Examples of the lubricant include talc and magnesium stearate. Furthermore, additives such as lactose and mannitol may also be used as long as they are used conventionally.

Moreover, the immunosuppressive substance of the present invention may be administered in the form of aerosol or inhalant, which is prepared by charging the active substance of liquid- or fine powder-form, together with a gaseous or liquid spraying agent, and, if necessary, a known auxiliary agent such as a wetting agent, into a non-pressurized container such as an aerosol container or a nebulizer. As the spraying agent, a pressurized gas, for example, dichlorofluoromethane, propane or nitrogen may be used.

For parenteral administration, the immunosuppressive substance of the present invention can be administered by injection, percutaneously, rectally or intraocularly.

For the administration by injection, the immunosuppressive substance of the present invention can be injected, for example, hypodermically, intracutaneously, intravenously or intramuscularly. An injection preparation may be formulated by dissolving, suspending or emulsifying the immunosuppressive substance of the present invention into an aqueous or non-aqueous solvent such as a vegetable oil, a synthetic glyceride with a fatty acid, an ester of a higher fatty acid or propylene glycol by a known method. If desired, a conventional additive such as a solubilizing agent, an osmoregulating agent, an emulsifier, a stabilizer or a preservative, may be added to the preparation.

For formulating the immunosuppressive substance of the present invention into solutions, suspensions, syrups or elixirs, a pharmaceutically acceptable solvent such as sterilized water for injection or a normalized physiological saline solution may be used.

For the percutaneous administration, the immunosuppressive substance of the present invention may be administered in the form of ointment, emulsifications, pastae, plasters, liniments, lotions, suspensions in accordance with the state of skin to be treated.

The ointments can be formulated by a known method by kneading the immunosuppressive substance of the present invention with a hydrophobic base, such as Vaseline or paraffin, or a hydrophilic bas, such as hydrophilic Vaseline or macrogol. The emulsifying agents and other percutaneous agents may be formulated by a method conventionally used.

For the rectal administration, a suppository can be used. The suppository may be prepared by mixing the immunosuppressive substance of the present invention with an excipient that can be melted at body temperature but is solid at room temperature, such as cacao butter, carbon wax or polyethylene glycol, and molding the resultant material, by a known method.

For the intraocular administration, ophthalmic formulations such as eye drops and eye ointments may be administered. The eye drops are formulated by dissolving or suspending the immunosuppressive substance of the present invention in an aqueous solvent, such as sterilized water, and, if necessary, adding a preservative, buffer, and surfactant.

The immunosuppressive substance of the present invention may be used together with a pharmaceutically acceptable compound having another activity, to prepare a pharmaceutical preparation.

The dose of the immunosuppressive substance of the present invention may be appropriately set or adjusted in accordance with an administration form, an administration route, a degree or stage of a target disease, and the like. For example, in the case of oral administration, a dose of the immunosuppressive substance may be set at 1–100 mg/kg body weight/day, preferably 1–10 mg/kg body weight/day. In the case of administration by injection, a dose of the immunosuppressive substance may be set at 1–50 mg/kg body weight/day, more preferably, 1–5 mg/kg body weight/day. In the case of percutaneous administration, a dose of the immunosuppressive substance may be set at 1–100 mg/kg body weight/day, more preferably, 1–10 mg/kg body weight/day. In the case of rectal administration, a dose of the immunosuppressive substance may be set at 1–50 mg/kg body weight/day, more preferably 1–5 mg/kg body weight/day. In the case of intraocular administration, about a 0.01–3% solution of the immunosuppressive substance may be applied dropwise to an eye several times per day. However, the doses are not limited to these.

The anticancer agent of the present invention contains, as an active ingredient, at least one β-sulfoquinovosylacylglycerol derivative represented by General formula (1-2) of the present invention and pharmaceutically acceptable salts thereof. Examples of the pharmaceutically acceptable salts employed in the anticancer agent of the present invention are the same as those mentioned for the immunosuppressive agent of the present invention, however, the salts are not limited to those. The administration routes may be the same as those mentioned for the immunosuppressive agent of the present invention.

The dose of the anticancer drug of the present invention may be appropriately set or adjusted in accordance with an administration form, an administration route, a degree or stage of a target disease, and the like. For example, in case of oral administration, administration by injection, or rectal administration, a dose may be set at 1–10 mg/kg body weight/day, 1–5 mg/kg body weight/day, or 1–5 mg/kg body weight/day, respectively, of an anticancer active substance of the present invention, but is not limited thereto.

The same administration routs, corresponding dosage forms thereof as those of the ainticancer drug of the invention can be applied to the DNA polymerase α inhibitor of the present invention.

EXAMPLES

The present invention will now be described by way of its Examples. However, the present invention is not limited to these Examples.

Synthesis examples of a sulfoquinovosylacylglycerol derivatives are set forth below, as examples of the active ingredients used in the immunosuppressive agent, anticancer agent and DNA polymerase α inhibitor of the present invention.

<Example 1>

Route a: 2,3,4,6-tetra-O-acetyl-D-glucopyranosyl bromide (II)

To 400 mL of acetic anhydride, 2.4 mL of 60% perchloric acid was added dropwise at 0° C. After the solution was returned to room temperature, 100 g (0.56 mol) of D-glucose was added to the solution with stirring for about 30 minutes while keeping the solution temperature at 30–40° C. After the reaction solution was cooled to 20° C., 30 g (1.0 mol) of red phosphorus was added. While the solution temperature was maintained at 20° C. or less, 180 g (2.3 mol) of bromine, and then 36 mL of water were added dropwise. After the resultant mixture was allowed to stand at room temperature for 2 hours, 300 mL of cold chloroform was added to the mixture. The reaction solution was filtrated by a funnel having a glass wool placed at the bottom. The filtrate was poured into cold water (800 mL) and a chloroform layer was separated by a separatory funnel. The water layer was extracted with 50 mL of chloroform. The chloroform layers were combined and washed with cold water (300 mL). The resultant chloroform layer was poured into 500 mL of saturated sodium hydrogencarbonate solution, sufficiently shaken in a separatory funnel. The resultant chloroform layer was recovered, dried over anhydrous sodium sulfate, filtrated, and concentrated in vacuo to give a crystalline substance. The obtained crystalline substance was pulverized in a mortar together with a solution of petroleum ether:ether (2:1) and filtered off. The crude crystalline substance was dried in vacuo, recrystallized with cold diisopropylether. As a result, a pure crystal was obtained (yield: 152.6 g, 0.37 mol, recovery: 66.7%).

Melting point: 88–90° C. Rf value: 0.338 (Hexan:ethyl acetate=4:1)

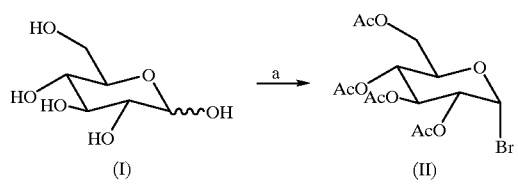

Route b: 2,3,4,6-tetra-O-acetyl-1-0-(2-propenyl)-β-D-glucose (III)

In 100 mL of allyl alcohol, 16.7 g (40.6 mmol) of the compound (II) was dissolved, and 10.0 g (39.6 mmol) of mercury cyanide was added thereto. The resultant mixture was stirred at room temperature overnight. The reaction solution was concentrated in vacuo, shaken together with 100 mL of chloroform and cold water in a separatory funnel to allow the chloroform layer to separate. After the chloroform layer was dried over anhydrous sodium sulfate, filtrated, and concentrated in vacuo, the resultant syrup was dissolved in cold diisopropylether. To the resultant solution, a small amount of crystal seed was added and stood in an ice-cooled condition. As a result, a crystal was obtained (yield: 12.6 g, 32.5 mmol, recovery: 80%)

Melting point: 77–81° C., Rf value: 0.282 (benzene: ethyl acetate=4:1)

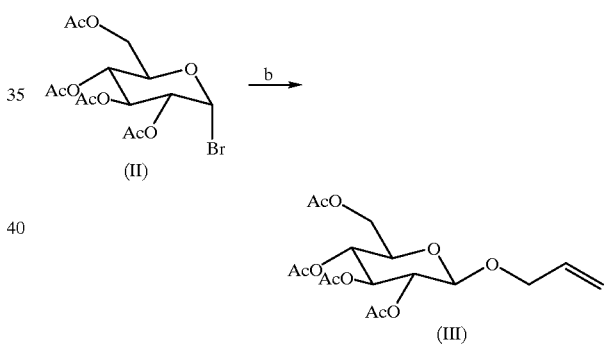

Route c: 1-0-(2-propenyl)-β-D-glucose (IV)

The compound (III)(30.3 g, 78.1 mmol) was dissolved in 120 mL of methanol. To the solution mixture, a small amount of 28% sodium methoxide in methanol was added dropwise while stirring. The reaction mixture was reacted at room temperature for 4 hours, neutralized with 0.1N hydrochloric acid, dried over anhydrous sodium sulfate, filtrated, concentrated in vacuo, and purified by silica gel flash chromatography (chloroform:methanol=4:1). As a result, a colorless and transparent oily substance was obtained (yield: 15.8 g, 71.8 mmol, recovery: 91.9%).

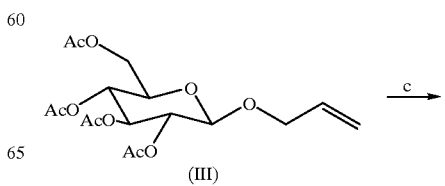

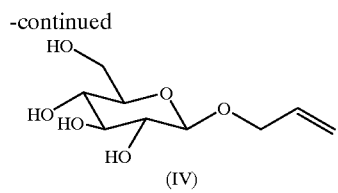

(IV)

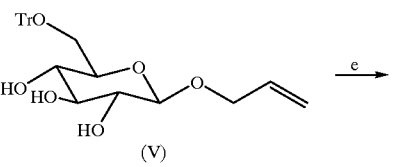

(V)

Route d: 1-O-(2-propenyl)-6-O-triphenylmethyl-β-D-glucose (V)

The compound (IV)(15.8 g, 71.8 mmol) was dissolved in 120 mL of anhydrous pyridine. To the solution, 23.4 g (83.9 mmol) of trityl chloride and 0.1 g (0.82 mmol) of p-dimethylaminopyridine (DMAP) were added. The reaction mixture was reacted for 36 hours at room temperature while stirring. Then, the reaction was quenched by adding 300 mL of cold water and the extracted with ethyl acetate (3×300 mL). The resultant organic layers were combined, neutralized with 1.0N hydrochloric acid to pH 4, washed with brine (2×300 mL), dried over anhydrous sodium sulfate, filtered, concentrated in vacuo, and purified by silica gel flash chromatography (dichloromethane:methanol= 20:1)). As a result, a pale yellowish oily substance was obtained (yield: 28.7 g, 62.1 mmol, recovery: 86.5%). Rf value: 0.306 (chloroform:methanol=19:1).

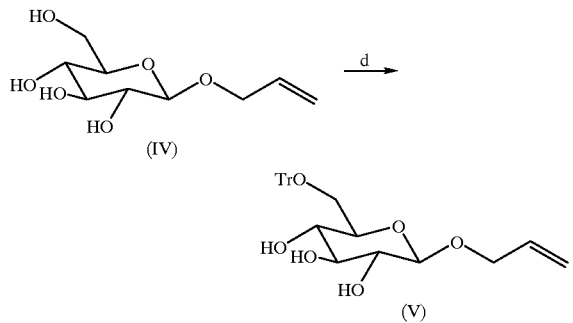

Route e: 2,3,4-tri-O-benzyl-1-O-(2-propenyl)-6-O-triphenylmethyl-β-D-glucose (VI)

80% sodium hydride (3.2 g, 133 mmol) dispersed in a mineral oil was put into a reaction vessel, and sufficiently washed with anhydrous hexane (50 mL). After the hexane was removed, 14.2 g (30.7 mmol) of the compound (V) dissolved in dry N,N-dimethylformamide was gradually added to the resultant suspension in an ice-cooled condition. After 15 minutes, the reaction mixture was returned to room temperature and the reaction was performed for one hour while stirring.

Next, 21.6 g (126 mmol) of benzylbromide were gradually added to the reaction mixture under an ice-cooled condition again. After 15 minutes, the reaction mixture was returned to room temperature, and reacted for 3 hours while stirring. Then, 20 mL of methanol and 30 mL of cold water were added to the reaction mixture to quench the reaction. The reaction mixture was extracted with ethyl acetate (3×50 mL). The organic layers were combined, washed with brine (2×100 mL), dried over anhydrous sodium sulfate, filtered, concentrated in vacuo, and purified by silica gel flash chromatography (hexane:ethyl acetate=10:1). As a result, a pale yellowish oily substance was obtained (yield: 21.6 g, 29.5 mmol, recovery: 96.1%). The Rf value: 0.410 (hexane:ethyl acetate=4:1)

Route f: 2,3,4-tri-O-benzyl-1-O-(2-propenyl)-β-D-glucose (VII)

In 150 mL of methanol, the compound (VI) (21.6 g, 29.5 mmol) was dissolved and 2.80 g (14.7 mmol) of p-toluenesulfonic acid monohydrate was added. The solution was reacted overnight while stirring. Thereafter, the reaction was quenched by adding 100 mL of cold water and extracted with ethyl acetate (3×200 mL). The organic layers were combined, washed with brine (2×300 mL), dried over anhydrous sodium sulfate, filtered, concentrated in vacuo, and purified to silica gel flash chromatography (hexane:ethyl acetate=4:1). As a result, a white crystalline substrate was obtained (yield 9.0 g, 18.4 mmol, recovery 62.4%).

Melting point: 80–82° C.,

Rf value: 0.338 (hexane:ethyl acetate=4:1) $[\alpha]_D$=+0.4° (c 5.50 CHCl$_3$)

$^1$H NMR (300 MHz, CDCl$_3$+TMS, δ); 7.36-7.23 (15H, m, Ar), 6.02-5.89 (1H, m, —CH═CH$_2$), 5.34 (1H, dd, J=1.5 & 17.2, —CH═CH$_2$), 5.22 (1H, dd, J=1.4 & 10.4, —CH═CH$_2$), 4.95 (1H, d, J=10.9, Ar—CH$_2$), 4.94 (1H, d, J=10.9, Ar—CH$_2$), 4.86 (1H, d, J=10.9, Ar—CH$_2$), 4.81 (1H, d, J=10.9, Ar—CH$_2$), 4.73 (1H, d, J=10.9, Ar—CH$_2$), 4.64 (1H, d, J=10.9, Ar—CH$_2$), 4.50 (1H, d, J=7.8, H-1), 4.43-4.13 (2H, m, —O—CH$_2$—CH═CH$_2$), 3.88-3.34 (6H, m, H-2 & H-3 & H-4 & H-5 & H-6a,b)

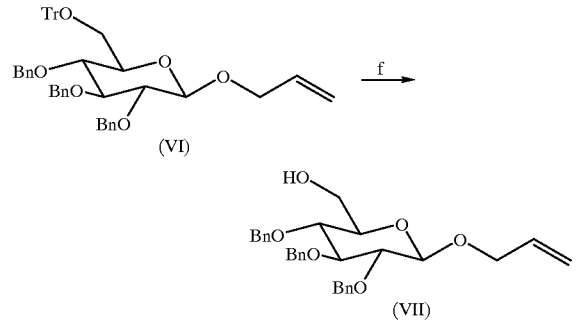

Route g: 2,3,4-tri-O-benzyl-1-O-(2-propenyl)-6-O-(4-tolylsulfonyl)-β-D-glucose (VIII)

In 200 mL of anhydrous pyridine, 9.80 g (20.0 mmol) of the compound (VII) was dissolved, and then 24.4 mg (0.2 mmol) of DMAP and 11.4 g(60.0 mmol) of p-toluenesulfonyl chloride were added. The solution was reacted at room temperature overnight while stirring. Thereafter, the reaction was quenched by adding 300 mL of cold water and extracted with ethyl acetate (3×200 mL). The resultant organic layers were combined, neutralized to pH 4 with 1.0N and 0.1N hydrochloric acid, washed with brine (2×300 mL), dried over anhydrous sodium sulfate, filtered, concentrated in vacuo, and purified by silica gel flash chromatography (hexane:ethyl acetate=4:1). As a result, a white crystalline substance was obtained (yield: 9.00 g, 14.0 mmol, recovery 70.0%).

Melting point: 111–112° C., Rf value: 0.295 (hexane:ethyl acetate=4:1)

$^1$H NMR (300 MHz, CDCl$_3$+TMS, δ); 7.77 (2H, d, J=8.2, H at Ts Me), 7.31-7.25 (15H, m, Ar), 7.19-7.16 (2H, m, H at Ts SO$_2$), 5.98-5.85 (1H, m, —CH═CH$_2$), 5.35-5.19 (2H, m, —CH═CH$_2$), 4.92 (2H, d, J=10.9, Ar—CH$_2$), 4.81 (1H, d, J=10.8, Ar—CH$_2$), 4.75 (1H, d, J=10.9, Ar—CH$_2$), 4.68 (2H, d, J=10.9, Ar—CH$_2$), 4.48 (1H, d, J=10.8, Ar—CH$_2$), 4.39 (1H, d, J=-7.8, H-1), 4.34-3.38 (8H, m, H-2 & H-3 & H-4 & H-5 & H-6a,b & —O—CH$_2$—CH═CH$_2$), 2.42 (3H, s, Ts CH$_3$)

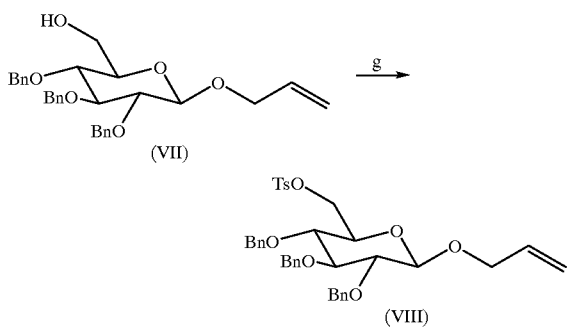

Route h: 2,3,4-tri-O-benzyl-1-O-(2-propenyl)-6-deoxy-6-acetylthio-β-D-glucose (IX)

In 250 mL of anhydrous ethanol, 9.00 g (14.0 mmol) of the compound (VIII) was dissolved and then 4.80 g (42.0 mmol) of potassium thioacetate was added. The solution was reacted under reflux for 3 hours while stirring. Thereafter, the reaction was quenched by adding 300 mL of cold water, and extracted with ethyl acetate (3×200 mL). The organic layers were combined, washed with brine (2×300 mL), dried over anhydrous sodium sulfate, filtered, concentrated in vacuo, purified by silica gel flash chromatography (hexane:ethyl acetate=10:1). As a result, a white crystalline substance was obtained (yield: 6.60 g, 12.0 mmol, recovery: 85.7%). Melting point: 70–73° C., Rf value: 0.295 (hexane:ethyl acetate=4:1) [α]$_D$=+26.7(c 0.75, CHCl$_3$)

$^1$H NMR (300 MHz, CDCl$_3$+TMS, δ); 7.35-7.25 (15H, m, Ar), 6.00-5.89 (1H, m, —CH═CH$_2$), 5.35 (1H, dd, J=1.5 & 17.2, —CH═CH$_2$), 5.22 (1H, dd, J=1.3 & 10.4, —CH═CH$_2$), 4.95 (1H, d, J=10.9, Ar—CH$_2$), 4.93 (1H, d, J=10.8, Ar—CH$_2$), 4.87 (1H, d, J=10.8, Ar—CH$_2$), 4.78 (1H, d, J=10.9, Ar—CH$_2$), 4.71 (1H, d, J=10.9, Ar—CH$_2$), 4.63 (1H, d, J=10.7, Ar—CH$_2$), 4.42 (1H, d, J=7.9, H-1), 4.37-3.33 (7H, m, H-2 & H-3 & H-4 & H-5 & H-6a & —O—CH$_2$—CH═CH$_2$), 2.96 (1H, dd, J=6.9 & 13.6, H-6b), 2.34 (3H, s, SCOCH$_3$)

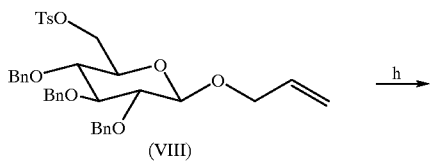

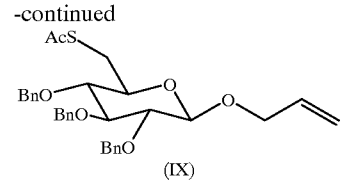

Route i: 3-0-(2,3,4-tri-O-benzyl-6-deoxy-6-acetylthio-β-D-glucopyranosyl)-glycerol (X)

In a mixture of t-butanol: H$_2$O (4:1), 3.30 g (6.02 mmol) of the compound (IX) was dissolved and then 1.34 g (12.1 mmol) of trimethylamine N-oxide dihydrate and 1.7 mL of 0.04 M solution of osmium tetraoxide in t-butanol were added. The solution was reacted at room temperature for 3 days while stirring. Thereafter, 5.8 g of activated charcoal was added, and then the reaction mixture was allowed to stand while stirring for 1.5 hours. After filtration with suction, the reaction was quenched by adding 250 mL of cold water and extracted with ethyl acetate (3×200 ml). The organic layers were combined, washed with brine (2×300 mL), dried over anhydrous sodium sulfate, filtered, concentrated in vacuo, and purified by silica gel flash chromatography (hexane:ethyl acetate=1:1). As a result, a white crystalline substance was obtained (yield: 1.79 g, 3.08 mmol, recovery 51.2%). Melting point: 91–93° C., Rf value: 0.112 (hexane:ethyl acetate=1:1), [α]$_D$=+18.0 (c 0.75, CHCl$_3$)

$^1$H NMR (300 MHz, CDCl$_3$+TMS, δ); 7.35-7.25 (15H, m, Ar), 4.94-4.61 (6H, m, Ar—CH$_2$), 4.38 (0.5H, d, J=7.8, H-1(R or S)), 4.37 (0.5H, d, J=7.8, H-1(R or S)), 3.83-3.37 (7H, m, H-2 & H-3 & H-4 & H-5 & H-6a & —O—CH$_2$—CH═CH$_2$), 2.96 (1H, dd, J=6.9 & 13.6, H-6b), 2.34 (3H, s, SCOCH$_3$)

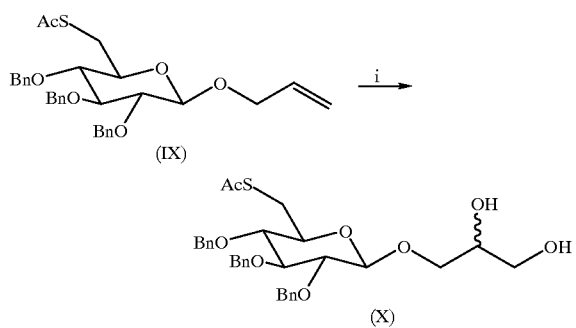

Route j: 3-O-(2,3,4-tri-O-benzyl-6-deoxy-6-acetylthio-β-D-glucopyranosyl)-1,2-di-O-stearoyl-glycerol (XI)

Into 100 mL of dichloromethane, 1.23 g (2.12 mmol) of the compound (X) was dissolved and then 1.30 g (6.79 mmol) of 1-ethyl-3-(3-dimethylaminopropyl)-carbodiimide hydrochloride (EDCI), 260 mg (2.13 mmol) of DMAP, and 1.75 g (6.15 mmol) of stearic acid, were added. The solution was reacted at room temperature for a day while stirring. Thereafter, the reaction was quenched by adding 100 mL of dichloromethane, washed with brine (2×50 mL), dried over anhydrous sodium sulfate, filtered, concentrated in vacuo, and purified by silica gel flash chromatography (hexane:ethyl acetate 10:1→8:1). As a result, a white non-crystalline solid substance was obtained (yield: 2.10 g, 1.88 mmol, recovery: 88.7%). Rf value: 0.487 (hexane; ethyl acetate=4:1) [α]$_D$=-21.3 (c 0.15, CHCl$_3$)

$^1$H NMR (300 MHz, CDCl$_3$+TMS, δ); 7.34-7.26 (15H, m, Ar), 5.28(1H, m, Gly-H-2), 4.92-4.60 (6H, m, Ar—CH$_2$), 4.36 (0.5H, d, J=7.7, H-1(R or S)), 4.35 (0.5H, d, J=7.8,

H-1(R or S)), 4.25-2.96 (10H, m, H-2 & H-3 & H-4 & H-5 & H-6a, b & Gly-H-1a, b & Gly-H-3a, b), 2.37 (1.5H, s, SCOCH₃(R or S)), 2.35 (1.5H, s, SCOCH₃(R or S)), 2.32-2.24(4H, m, OCOCH₂), 1.65-1.58 (4H, m, OCOCH₂CH₂), 1.25 (56H, br, —CH₂—), 0.88 (6H, t, J=6.3, CH₃)

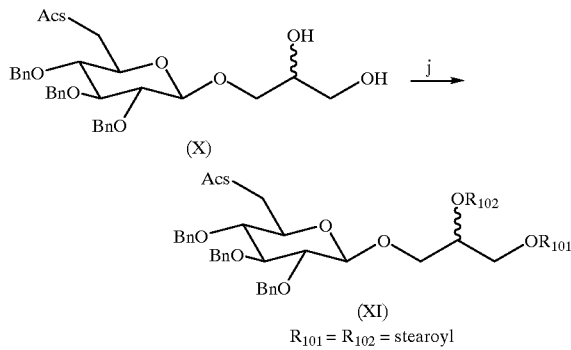

Route k: 3-O-(2,3,4-tri-O-benzyl-6-deoxy-6-sulfo-β-D-glucopyranosyl)-1,2-di-O-stearoyl-glycerol sodium salt (XII)

In 50 mL of acetic acid, 1.24 g (1.11 mmol) of the compound (XI) was dissolved and then 1.5 g of potassium acetate and 1.55 g of OXONE (2KHSO₅, KHSO₄, K₂SO₄) were added. The solution was reacted overnight at room temperature while stirring. Thereafter, the reaction was quenched by adding 100 mL of cold water, and extracted with ethyl acetate (5×50 mL). The organic layers were combined, neutralized with saturated sodium hydrogencarbonate (2×100 mL), washed with brine (2×100 mL), dried over anhydrous sodium sulfate, filtered, concentrated in vacuo, and purified by silica gel flash chromatography (chloroform:methanol=20:1→15:1). As a result, a white non-crystalline solid substance was obtained (yield: 773 mg, 0.677 mmol, recovery 61.0%). Rf value: 0.288 (dichlormethane:methanol=10:1), $[\alpha]_D$=+4.8° (c 0.17, CHCl₃)

¹H NMR (300 MHz, CDCl₃+TMS, δ); 7.29-7.16 (15H, m, Ar), 5.31(1H, m, Gly-H-2), 4.91-4.56 (6H, m, Ar—CH₂), 4.50 (1H, d, J=7.6, H-1), 4.44-3.03 (10H, m, H-2 & H-3 & H-4 & H-5 & H-6a, b & Gly-H-1a, b & Gly-H-3a, b), 2.62(4H, br, OCOCH₂), 2.19-2.17 (4H, br, OCOCH₂CH₂), 1.49 (4H, br, OCOCH₂CH₂CH₂), 1.25 (52H, br, —CH₂—), 0.88 (6H, t, J=6.3, CH₃)

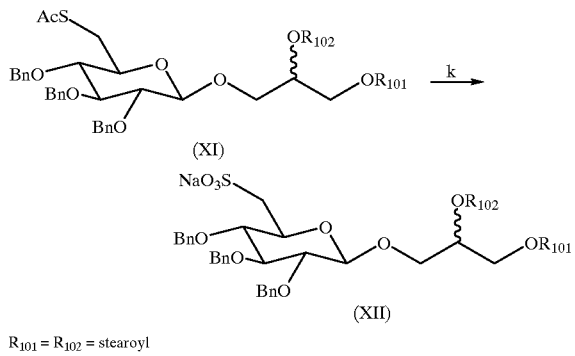

Route 1: 3-O-(6-deoxy-6-sulfo-β-D-glucopyranosyl)-1,2-di-O-stearoyl-glycerol sodium salt (XIII)

Into 50 mL of ethanol, 773 mg (0.677 mmol) of the compound (XII) was dissolved and then 2.00 g of 10% palladium-activated carbon (Pd-C) was added. After the atmosphere of the flask was substituted with hydrogen, the solution mixture was reacted at room temperature overnight while stirring. Then, the reaction mixture was filtered with suction using celite, concentrated in vacuo, and purified by silica gel flash chromatography (chloroform:methanol=10:1→chloroform:methanol:water=70:30:4). As a result, a white non-crystalline solid substance was obtained (yield: 311 mg, 0.356 mmol, recovery 52.6%).

Rf value: 0.402 (chloroform:methanol:water=65:25:4), $[\alpha]_D$=−3.6° (c 0.59, CHCl₃: CH₃OH:H₂O=70:30:4).

¹H NMR (300 MHz, CDCl₃+TMS, δ); 5.28(1H, m, Gly-H-2), 4.32 (1H, d, J=7.7, H-1), 4.27-3.11 (10H, m, H-2 & H-3 & H-4 & H-5 & H-6a, b & Gly-H-1a, b & Gly-H-3a, b), 2.36-2.30(4H, m, OCOCH₂), 1.60 (4H, m, OCOCH₂CH₂), 1.27 (56H, br, —CH₂—), 0.89 (6H, t, J=6.4, CH₃)

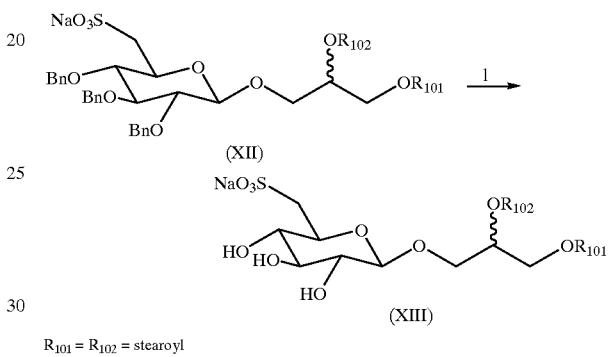

<Example 2: Synthesis of 2, 3, 4-tri-O-benzyl-1-O-(2-propenyl)-6-O-(4-tolylsulfonyl)-α-D-glucose (VI)>

Starting from D-glucose, 2,3,4-tri-O-benzyl-1-O-(2-propenyl)-6-O-(4-tolylsulfonyl)-α-D-glucose (VI) was prepared as follows.

2-1) Step a: Synthesis of 1-O-(2-propenyl)-D-glucose (II)

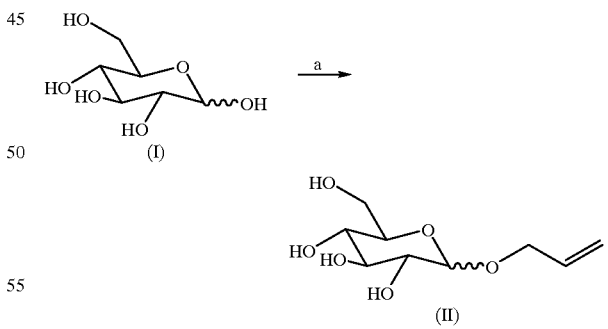

One hundred grams of D-glucose (I) were added into 250 mL of allyl alcohol and sufficiently dissolved therein. To the solution, 0.8 mL of trifluoromethanesulfonic acid were slowly added under an ice-cooled condition. Then, the solution was reacted in an oil bath at 80° C. for 30 hours, while stirring. Then the reaction mixture was neutralized with 1 mL of triethylamine, and was concentrated in vacuo to give the title compound. Thin layer chromatography demonstrated a yield of about 60–70%.

2-2) Step b: Synthesis of 1-O-(2-propenyl)-6-O-triphenylmethyl-D-glucose (III).

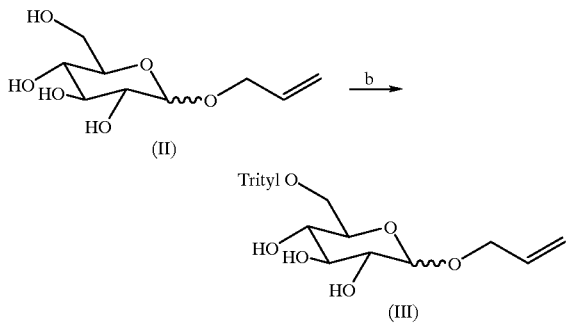

One hundred grams (455 mmol) of 1-O-(2-propenyl)-D-glucose (II) were dissolved in 350 mL of anhydrous pyridine, and the solution was added with 170 g (610 mmol) of tritylchloride and 1.0 g (8.20 mmol) of DMAP. The reaction mixture was reacted for 36 hours at room temperature, while stirring. Then, the reaction was quenched by addition of 800 mL of cold distilled water, and then extracted with ethyl acetate (3×500 mL). The organic layers were combined, acidified to pH 4 by diluted hydrochloric acid, washed with saturated aqueous sodium chloride (2×500 mL), dried over anhydrous sodium sulfate, filtered, concentrated in vacuo, and purified by silica gel flash chromatography (dichloromethane:methanol=20:1) to give the title compound. Thin layer chromatography demonstrated a yield of about 80%.

2-3) Step c: Synthesis of 2,3,4-tri-O-benzyl-1-O-(2-propenyl)-6-O-triphenylmethyl-D-glucose (IV)

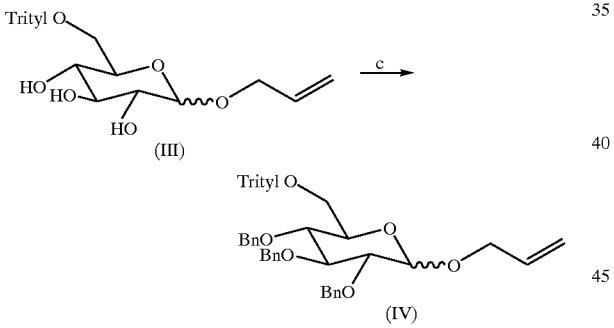

Two grams (83.3 mmol) of 80% sodium hydride dispersed in a mineral oil were put into a reactor, and were sufficiently washed with 50 mL of anhydrous hexane. Then, the hexane was removed from the reactor, to which 10.0 g (21.6 mmol) of 1-O-(2-propenyl)-6-O-triphenylmethyl-D-glucose (III) were slowly added under an ice-cooled condition. After 15 minutes, the reaction mixture was returned to room temperature, and reacted for 1 hour while stirring.

Next, 12.0 g (70.2 mmol) of benzylbromide were slowly added to the reaction mixture again under an ice-cooled condition. After 15 minutes, the reaction mixture was returned to room temperature, and was reacted for 3 hours while stirring. Then, 20 mL of methanol and 30 mL of cold distilled water were added to the reaction mixture to quench the reaction, and the reaction mixture was extracted with ethyl acetate (3×50 mL). The organic layers were combined, washed with saturated aqueous sodium chloride (100 mL×2 times), dried over anhydrous sodium sulfate, filtered, concentrated in vacuo, and purified by silica gel flash chroma- tography (hexane:ethyl acetate=10:1) to give 9.6 g (13.8 mmol) of the title compound. Yield: 63.9%.

2-4) Step d: Synthesis of 2,3,4-tri-O-benzyl-1-O-(2-propenyl)-α-D-glucose (V)

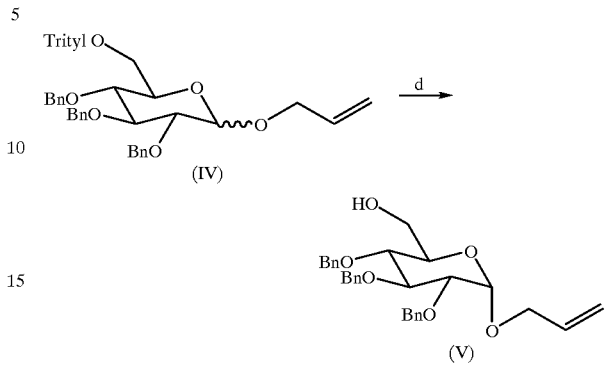

Into 100 mL of methanol, 9.6 g (13.8 mmol) of 2,3,4-tri-O-benzyl-1-O-(2-propenyl)-6-O-triphenylmethyl-D-glucose (IV) were dissolved, and 3.8 g (20.0 mmol) of p-toluenesulfonic acid monohydrate were added. The solution was reacted for 16 hours while stirring. Then, the reaction was quenched by adding 100 mL of cold distilled water, and the reaction mixture was extracted with ethyl acetate (3×200 mL). The organic layers were combined, washed with saturated aqueous sodium chloride (2×300 mL), dried over anhydrous sodium sulfate, filtered, concentrated in vacuo, and applied to silica gel flash chromatography (hexane:ethyl acetate=11:2→4:1→2:1), separating and purifying α- and β-anomers. The α-anomer in 2.70 g (5.50 mmol) with yield of 39.8%; and the β-anomer in 1.52 g (3.10 mmol) with yield of 22.5%.

2-5) Step e: Synthesis of 2, 3, 4-tri-O-benzyl-1-O-(2-propenyl)-6-O-(4-tolylsulfonyl)-α-D-glucose (VI)

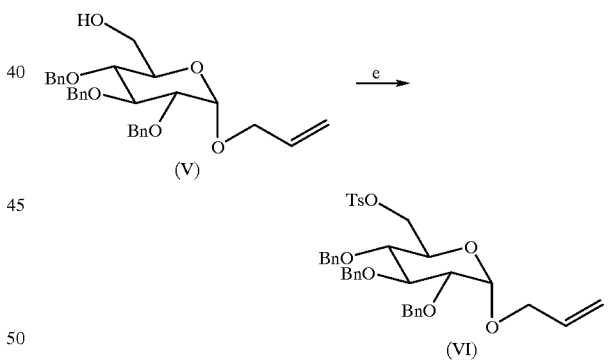

Into 200 mL of anhydrous pyridine, 10.0 g (20.4 mmol) of 2,3,4-tri-O-benzyl-1-O-(2-propenyl)-α-D-glucose (V) were dissolved, and then 134 mg (1.10 mmol) of DMAP and 9.2 g (48.3 mmol) of p-toluenesulfonyl chloride were added. The solution was reacted for 16 hours at room temperature while stirring. Then, the reaction was quenched by adding 300 mL of cold distilled water, and the reaction mixture was extracted with ethyl acetate (3×200 mL). The resultant organic layers were combined, acidified to pH 4 with diluted hydrochloric acid, washed with saturated aqueous sodium chloride (2×300 mL), dried over anhydrous sodium sulfate, filtered, concentrated in vacuo, and purified by silica gel flash chromatography (hexane:ethyl acetate=4:1) to give 12.0 g (18.6 mmol) of the tile compound with yield of 91.2%.

Melting point: 77–79° C.; $[\alpha]_D$=+51.8 (CHCl$_3$).

TABLE 2

| Absorption Peak (cm$^{-1}$) | Structure |
|---|---|
| 1940, 1860, 1800 | Mono-substituted Ar* |
| 1615 | Terminal double bond |
| 1593, 1480 | Ar* |
| 1170–1120, 1100–1000 | CO |
| 1180 | SO$_3$ |
| 910, 830 | α-Hexose characteristic absorption |

*Ar represents aromatics.

<Example 3: Synthesis of 2,3,4-tri-O-(t-butyldimethylsilyl)-1-O-(2-propenyl)-6-O-(4-tolylsulfonyl)-α-D-glucose (VI')>

Starting from D-glucose (I'), 2,3,4-tri-O-(t-butyldimethylsilyl)-1-O-(2-propenyl)-6-O-(4-tolylsulfonyl)-α-D-glucose (VI') was synthesized through the following steps a'–e'.

3-1) Step a': Synthesis of 1-O-(2-propenyl)-D-glucose (II')

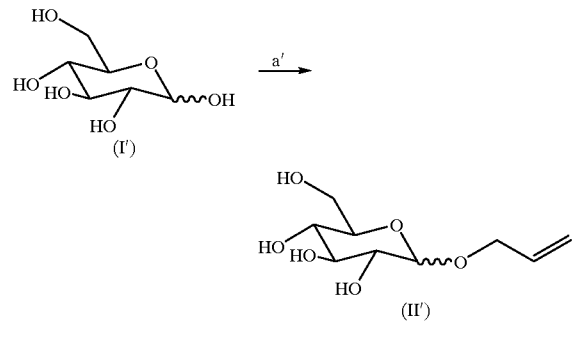

One hundred grams of D-glucose (I') were added to 250 mL of allyl alcohol and sufficiently dissolved therein. To the solution, 0.8 mL of trifluoromethanesulfonic acid were slowly added under an ice-cooled condition. Then, the solution was reacted in an oil bath at 80° C. for 30 hours while stirring. Then, the reaction mixture was neutralized by 1 mL of triethylamine, and was concentrated in vacuo to give the title compound. Thin layer chromatography demonstrated a yield of about 60–70%.

3-2) Step b': Synthesis of 1-O-(2-propenyl)-4,6-O-benzylidene-α-D-glucose (III')

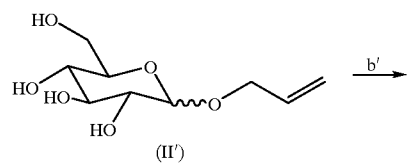

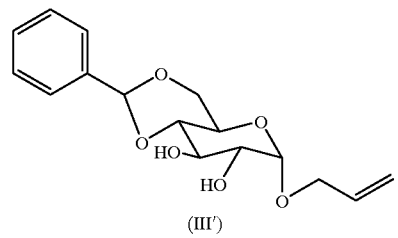

37.5 grams of 1-O-(2-propenyl)-D-glucose (II') were dissolved in 210 mL of benzaldehyde, and to the solution 98 g of zinc chloride were added. The reaction mixture was reacted at room temperature for 4 hours. Thereafter, the reaction mixture was added to 500 mL of hexane, and then 100 mL of diluted sodium hydrogencarbonate were added. The reaction mixture was allowed to stand at 0° C. for 30 minutes to be crystallized. The crystals were filtered with suction, and was dissolved into 50 mL of ethanol. The solution was allowed to stand at 0° C. for 30 minutes for recrystallization to give 21 g (68.1 mmol) of the title compound with yield of 40.0%.

3-3) Step c': Synthesis of 1-O-(2-propenyl)-α-D-glucose (IV')

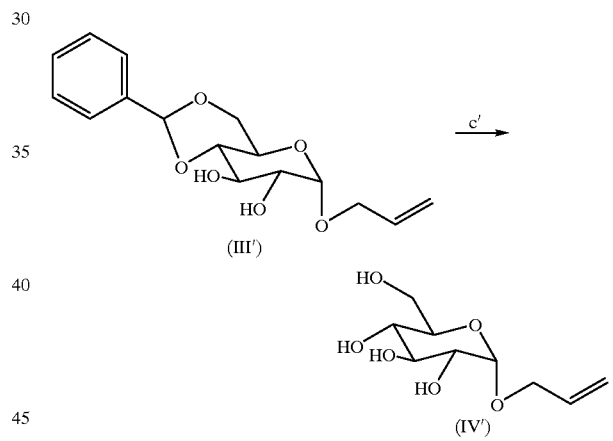

Into 260 mL of a solution of acetic acid and water (8:5), 10.7 g (34.7 mmol) of 1-O-(2-propenyl)-4,6-O-benzylidene-α-D-glucose (III') were dissolved. The solution was reacted at 100° C. for 1 hour, concentrated in vacuo, and purified by silica gel flash chromatography (dichloromethane:methanol=6:1) to give 6.3 g (28.6 mmol) of the title compound with yield of 82.4%.

3-4) Step d': Synthesis of 1-O-(2-propenyl)-6-O-(4-tolylsulfonyl)-α-D-glucose (V')

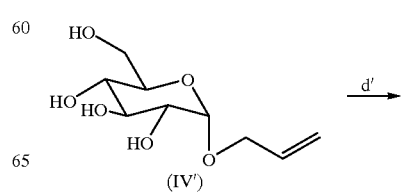

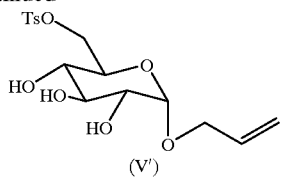

Into 200 mL of anhydrous pyridine, 6.3 g (28.6 mmol) of 1-O-(2-propenyl)-α-D-glucose (IV') were dissolved, and 195 mg of DMAP and 7.0 g of p-toluenesulfonyl chloride were added. The solution was reacted for 16 hours at room temperature while stirring. Thereafter, the reaction was quenched by adding 20 mL of cold distilled water, and the reaction mixture was extracted with ethyl acetate (3×200 mL). The organic layers were combined, acidified to pH 4 with 1.0 N and 0.1 N hydrochloric acids, washed with saturated aqueous sodium chloride (2×200 mL), dried over anhydrous sodium sulfate, filtered, concentrated in vacuo, and purified by silica gel flash chromatography (dichloromethane:methanol=20:1) to give 8.6 g (24.0 mmol) of the title compound with yield of 83.8%.

3-5) Step e': Synthesis of 2,3,4-tri-O-(t-butyldimethylsilyl)-1-O-(2-propenyl)-6-O-(4-tolylsulfonyl)-α-D-glucose (VI')

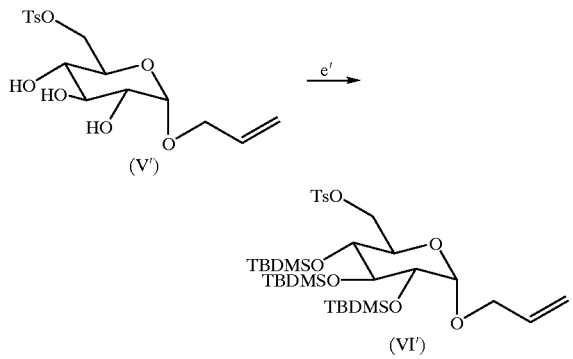

Into 25 mL of anhydrous dichloromethane, 11.2 g (29.9 mmol) of 1-O-(2-propenyl)-6-O-(4-tolylsulfonyl)-α-D-glucose (V') were dissolved and 23.8 g of t-butyldimethylsilyl trifluoromethanesulfonate and 14.4 g of 2,6-lutidine were added. The solution was reacted under nitrogen flow for 16 hours while stirring. Thereafter, the reaction was quenched by adding 150 mL of dichloromethane, and the reaction mixture was washed with saturated aqueous sodium chloride (2×100 mL), dried over anhydrous sodium sulfate, filtered, concentrated in vacuo, purified by silica gel flash chromatography (hexane:ethyl acetate=30:1) to give 19.6 g (27.4 mmol) of the title compound as a colorless and transparent oil. Yield of 91.6%. $[\alpha]_D=+39.0°$ (CHCl$_3$).

TABLE 3

| IR DATA | |
| --- | --- |
| Absorption Peak (cm$^{-1}$) | Structure |
| 1735, 1590, 1475 | Ar |
| 1105–1000, 950 | CO |
| 1160 | SO$_3$ |

TABLE 3-continued

| IR DATA | |
| --- | --- |
| Absorption Peak (cm$^{-1}$) | Structure |
| 930, 825, 770 | α-Hexose characteristic absorption |

<Example 4: Synthesis of 2,3,4-tri-O-benzyl-1-O-(2-propenyl)-6-deoxy-6-acetylthio-α-D-glucose (VII)>

From 2,3,4-tri-O-benzyl-1-O-(2-propenyl)-6-O-(4-tolylsulfonyl)-α-D-glucose (VI) obtained in Example 2, is 2,3,4-tri-O-benzyl-1-O-(2-propenyl)-6-deoxy-6-acetylthio-α-D-glucose (VII) was synthesized by the step f.

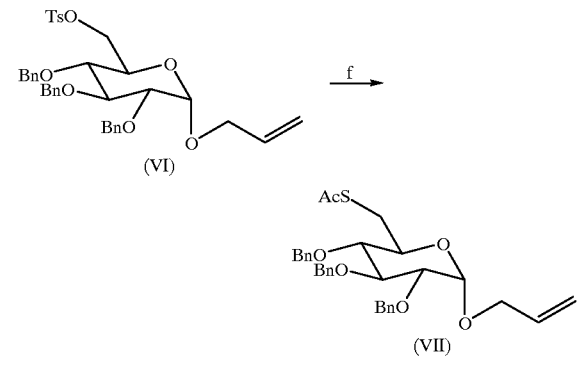

Into 250 mL of anhydrous ethanol, 11.4 g (18.6 mmol) of 2,3,4-tri-O-benzyl-1-O-(2-propenyl)-6-O-(4-tolylsulfonyl)-α-D-glucose (VI) were dissolved and then 5.6 g (49.0 mmol) of potassium thioacetate were added. The solution was reacted under reflux for 3 hours while stirring. Thereafter, the reaction was quenched by adding 300 mL of cold distilled water, and the reaction mixture was extracted with ethyl acetate (3×200 mL). The organic layers were combined, washed with saturated aqueous sodium chloride (2×300 mL), dried over anhydrous sodium sulfate, filtered, concentrated in vacuo, purified by silica gel flash chromatography (hexane:ethyl acetate=10:1) to give 9.00 g (16.4 mmol) of the title compound with yield of 88.2%. Melting point: 61–62.5° C.; $[\alpha]_D=+51.8°$ (CHCl$_3$).

TABLE 4

| IR DATA | |
| --- | --- |
| Absorption Peak (cm$^{-1}$) | Structure |
| 1940, 1880, 1800 | Mono-substituted Ar |
| 1680 | SCOCH$_3$ |
| 1600, 1580, 1490 | Ar |
| 1160–1120, 1090–1060 | CO |
| 1180 | SO$_3$ |
| 905, 830 | α-Hexose characteristic absorption |

<Example 5: Synthesis of 2,3,4-tri-O-(t-butyldimethylsilyl)-1-O-(2-propenyl)-6-deoxy-acetylthio-α-D-glucose (VII')>

From 2,3,4-tri-O-(t-butyldimethylsilyl)-1-O-(2-propenyl)-6-O-(4-tolylsulfonyl)-α-D-glucose (VI') obtained in Example 3, 2,3,4-tri-O-(t-butyldimethylsilyl)-1-O-(2-propenyl)-6-deoxy-acetylthio-α-D-glucose (VII') was synthesized by the step f'.

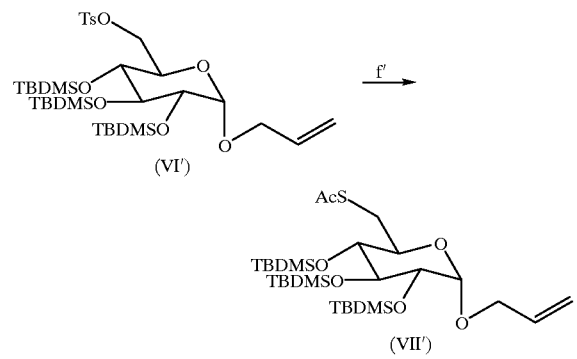

Into 20 mL of anhydrous ethanol, 7.9 g (11.0 mmol) of 2,3,4-tri-O-(t-butyldimethylsilyl)-1-O-(2-propenyl)-6-O-(4-tolylsulfonyl)-α-D-glucose (VI') were dissolved, and then 1.8 g of potassium thioacetate were added. The solution was reacted under reflux for 3 hours while stirring. Thereafter, the reaction was quenched by adding 100 mL of cold distilled water, and the reaction mixture was extracted with ethyl acetate (3×200 mL). The organic layers were combined, washed with saturated aqueous sodium chloride (2×200 mL), dried over anhydrous sodium sulfate, filtered, concentrated in vacuo, and purified by silica gel flash chromatography (hexane:ethyl acetate=50:1) to give 5.6 g (9.02 mmol) of the title compound as a colorless and transparent oily material. Yield of 82.0%. $[\alpha]_D = +60.9°$ ($CHCl_3$).

TABLE 5

IR DATA

| Absorption Peak (cm$^{-1}$) | Structure |
|---|---|
| 1670 | $SCOCH_3$ |
| 1620 | Terminal double bond |
| 1140–1000 | CO |
| 910, 810, 755 | α-Hexose characteristic absorption |

<Example 6: Synthesis of 3-O-(6-deoxy-6-sulfo-α-D-glucopyranosyl)-1,2-di-O-palmitoyl-glycerol sodium salt (XI-1) and 3-O-(6-deoxy-6-sulfo-α-D-glucopyranosyl)-1-O-palmitoyl-glycerol sodium salt (XI-2)>

From 2,3,4-tri-O-benzyl-1-O-(2-propenyl)-6-deoxy-6-acetylthio-α-D-glucose (VII) obtained in Example 4, a sulfoquinovosylacylglycerol derivative was synthesized through the steps g–j.

6-1) Step g: Synthesis of 3-O-(2,3,4-tri-O-benzyl-6-deoxy-6-acetylthio-α-D-glucopyranosyl)-glycerol (VIII)

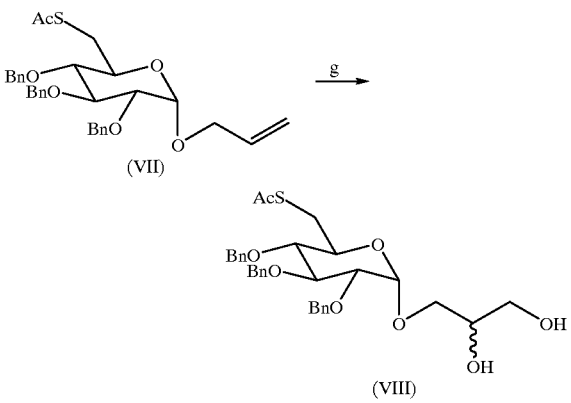

In a mixture of t-butanol and $H_2O$ (=4:1), 8.30 g (15.1 mmol) of 2,3,4-tri-O-benzyl-6-deoxy-1-O-(2-propenyl)-6-acetylthio-α-D-glucose (VII) were dissolved and then 2.5 g (22.5 mmol) of trimethylamine N-oxide dihydrate and 20 mL (0.04 M) of a t-butanol solution of osmium tetraoxide were added. The solution was reacted at room temperature for 30 hours while stirring. Thereafter, 15 g of activated carbon were added, and then the reaction mixture was allowed to stand while stirring for 1.5 hours to adsorb the osmium tetraoxide on the activated carbon. After filtration with suction, the reaction was quenched by adding 250 mL of cold distilled water, and the reaction mixture was extracted with ethyl acetate (3×200 ml). The organic layers were combined, washed with saturated aqueous sodium chloride (2×300 mL), dried over anhydrous sodium sulfate, filtered, concentrated in vacuo, and purified by silica gel flash chromatography (hexane:ethyl acetate=1:1) to give 5.00 g (8.59 mmol) of the title compound with yield of 56.9%.

6-2) Step h: Synthesis of 3-O-(2,3,4-tri-O-benzyl-6-deoxy-6-acetylthio-α-D-glucopyranosyl)-1,2-di-O-palmitoyl-glycerol (IX-1) and 3-O-(2,3,4-tri-O-benzyl-6-deoxy-6-acetylthio-α-D-glucopyranosyl)-1-O-palmitoyl-glycerol (IX-2)

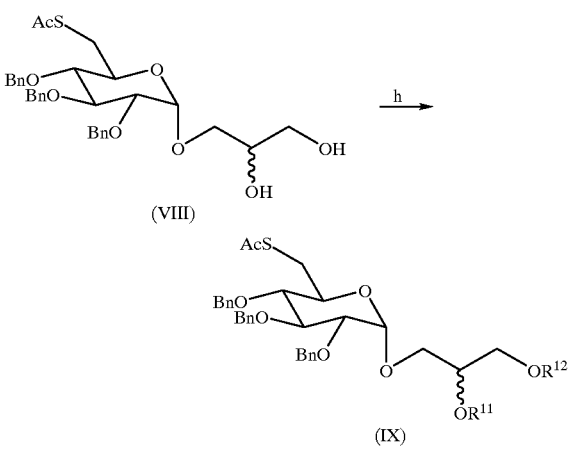

where IX-1: $R^{11}=R^{12}$=palmitoyl; IX-2: $R^{11}$=H, $R^{12}$=palmitoyl.

Into 5 mL of dichloromethane, 20.3 mg (34.3 μmol) of 3-O-(2,3,4-tri-O-benzyl-6-deoxy-6-acetylthio-α-D-glucopyranosyl)-glycerol (VIII) were dissolved and then 19.4 g (101 μmol) of EDCl, 5.70 mg (46.7 μmol) of DMAP, and 14.1 g (54.9 μmol) of palmitic acid were added. The solution was reacted at room temperature for 16 hours while stirring. Thereafter, the reaction was quenched by adding 20 mL of dichloromethane, and the reaction mixture was washed with saturated aqueous sodium chloride (2×20 mL), dried over anhydrous sodium sulfate, filtered, concentrated in vacuo, and applied to silica gel flash chromatography (hexane:ethyl acetate=7:1→3:1) to separate and purify the diester and monoester. The diester was obtained in 14.7 mg (13.9 μmol), while the monoester was obtained in 9.10 mg (11.1 μmol), with yield (total of both the esters) of 72.9%.

6-3-1) Step i-1: Synthesis of 3-O-(2,3,4-tri-O-benzyl-6-deoxy-6-sulfo-α-D-glucopyranosyl)-1,2-di-O-palmitoyl-glycerol sodium salt (X-1)

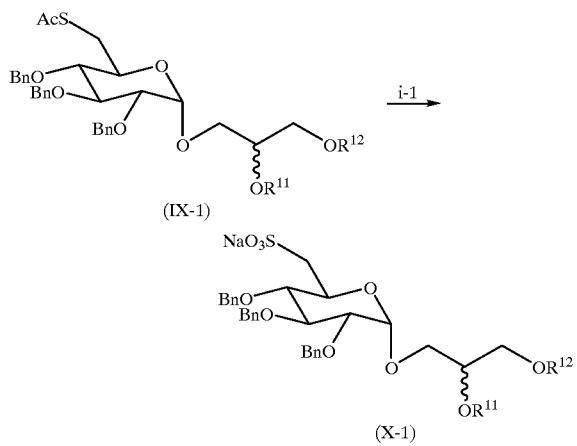

where $R^{11}=R^{12}$=palmitoyl.

Into 7 mL of glacial acetic acid, 133 mg (125 μmol) of 3-O-(2,3,4-tri-O-benzyl-6-deoxy-6-acetylthio-α-D-glucopyranosyl)-1,2-di-O-palmitoyl-glycerol (IX-1) were dissolved and then 814 mg of potassium acetate and 228 mg of OXONE were added. The solution was reacted for 16 hours at room temperature while stirring. Thereafter, the reaction was quenched by adding 20 mL of cold distilled water, and the reaction mixture was extracted with ethyl acetate (5×20 mL ). The organic layers were combined, neutralized with saturated sodium hydrogencarbonate (5×70 mL ), washed with saturated aqueous sodium chloride (2×60 mL), dried over anhydrous sodium sulfate, filtered, concentrated in vacuo, and purified by silica gel flash chromatography (dichloromethane:methanol=10:1) to give 57.9 mg (13.9 μmol) of the title compound with yield of 43.4%.

6-3-2) Step i-2: Synthesis of 3-O-(2,3,4-tri-O-benzyl-6-deoxy-6-sulfo-α-D-glucopyranosyl)-1-O-palmitoyl-glycerol sodium salt (X-2)

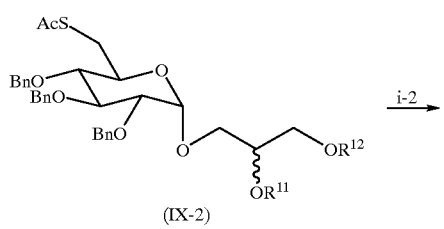

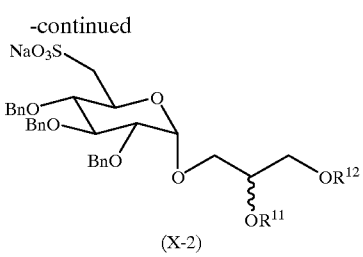

where $R^{11}$=H, $R^{12}$=palmitoyl.

Into 2 mL of glacial acetic acid, 52.1 mg (63.5 μmol) of 3-O-(2,3,4-tri-O-benzyl-6-deoxy-6-acetylthio-α-D-glucopyranosyl)-1-O-palmitoyl-glycerol (IX-2) were dissolved and then 102 mg of potassium acetate and 116 mg of OXONE were added. The solution was reacted at room temperature for 16 hours while stirring. Thereafter, the reaction was quenched by adding 15 mL of cold distilled water, and the reaction mixture was extracted with ethyl acetate (5×20 mL). The organic layers were combined, neutralized with saturated sodium hydrogencarbonate (5×70 mL), washed with saturated aqueous sodium chloride (2×60 mL), dried over anhydrous sodium sulfate, filtered, concentrated in vacuo, and purified by silica gel flash chromatography (dichloromethane:methanol=10:1) to give 35.1 mg (42.4 μmol) of the tile compound with yield of 66.8%.

6-4-1) Step j-1: Synthesis 3-O-(6-deoxy-6-sulfo-α-D-glucopyranosyl)-1,2-di-O-palmitoyl-glycerol sodium salt (XI-1)

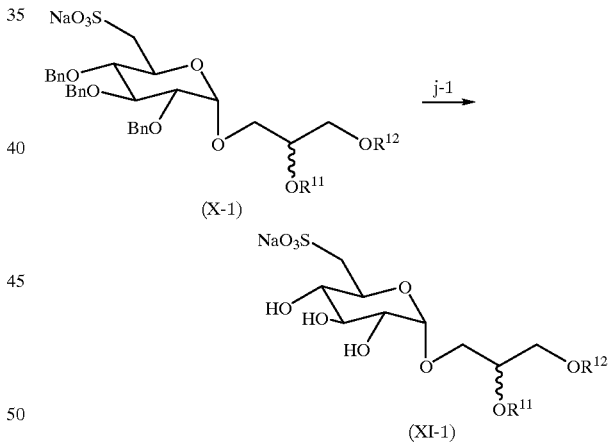

where $R^{11}$, $R^{12}$=palmitoyl.

Into 50 mL of ethanol, 359 mg (330 μmol) of a sodium salt of 3-O-(2,3,4-tri-O-benzyl-6-deoxy-6-sulfo-α-D-glucopyranosyl)-1,2-di-O-palmitoyl-glycerol(X-1) were dissolved and then 1.30 g of Pd-C were added. After substitution of the atmosphere in the flask with $H_2$, the solution mixture was reacted at room temperature for 16 hours while stirring. Then, the reaction mixture was filtered with suction, concentrated in vacuo, and purified by silica gel flash chromatography (dichloromethane methanol= 10:1→dichloromethane:methanol:water=65:25:4) to give 129 mg (168 μmol) of the title compound with yield of 50.9%.

6-4-2) Step j-2: Synthesis of 3-O-(6-deoxy-6-sulfo-α-D-glucopyranosyl)-1-O-palmitoyl-glycerol sodium salt (XI-2)

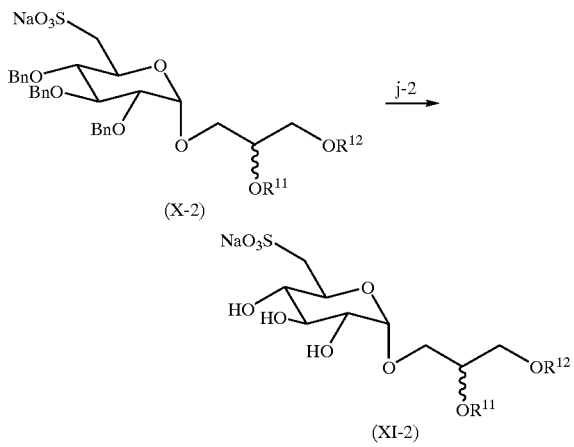

where $R^{11}$=H, $R^{12}$=palmitoyl.

Into 25 mL of ethanol, 202 mg (238 μmol) of a sodium salt of 3-O-(2,3,4-tri-O-benzyl-6-deoxy-6-sulfo-α-D-glucopyranosyl)-1-O-palmitoyl-glycerol (X-2) were dissolved and then 1.00 g of Pd-C was added. After substitution of the atmosphere in the flask with $H_2$, the solution was reacted at room temperature for 16 hours while stirring. Thereafter, the reaction mixture was filtered with suction, concentrated in vacuo, and purified by silica gel flash chromatography (dichloromethane:methanol= 10:1→dichloromethane:methanol:water=65:25:4) to give 57.2 mg (168 μmol) of the title compound with yield of 43.3%.

<Example 7: Synthesis of 3-O- (6-deoxy-6-sulfo-α-D-glucopyranosyl)-1,2-di-O-oleoyl-glycerol sodium salt (XI'-1) and 3-O- (6-deoxy-6-sulfo-α-D-glucopyranosyl)-1-O-oleoyl-glycerol sodium salt (XI'-2)>

From 2,3,4-tri-O-(t-butyldimethylsilyl)-6-deoxy-1-O-(2-propenyl)-6-acetylthio-α-D-glucose (VII') obtained in Example 5, a sulfoquinovosylacylglycerol derivative was synthesized through the steps g'–j'.

7-1) Step g': Synthesis of 3-O-[2,3,4-tri-O-(t-butyldimethylsilyl)-6-deoxy-6-acetylthio-α-D-glucopyranosyl]-glycerol (VIII')

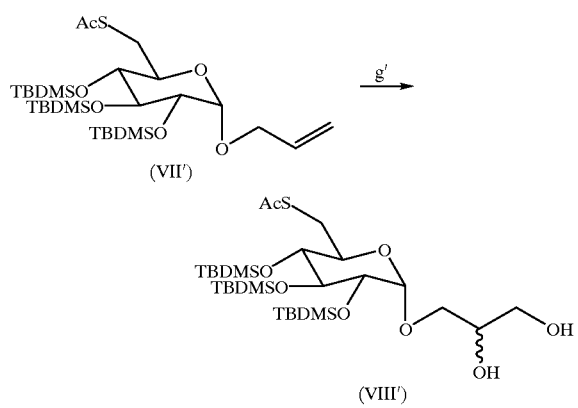

Into a mixture of t-butanol and $H_2O$ (=4:1), 5.6 g (9.02 mmol) of 2,3,4-tri-O-(t-butyldimethylsilyl)-6-deoxy-1-O-(2-propenyl)-6-acetylthio-α-D-glucose (VII') were dissolved and then 1.5 g of trimethylamine N-oxide dihydrate and 15 mL (0.04 M) of a t-butanol solution of osmium tetraoxide were added. The solution was reacted at room temperature for 22 hours while stirring. Thereafter, 15 g of activated carbon were added, and the reaction mixture was allowed to stand while stirring for 1.5 hours to adsorb the osmium tetraoxide on the activated carbon. After filtration with suction, the reaction was quenched by adding 200 mL of cold distilled water, and the reaction mixture was extracted with ethyl acetate (3×200 mL). The organic layers were combined, washed with saturated aqueous sodium chloride (2×300 mL), dried over anhydrous sodium sulfate, filtered, concentrated in vacuo, and purified by silica gel flash chromatography (hexane:ethyl acetate=3:1→2:1) to give 5.2 g (7.94 mmol) of the title compound with yield of 88.0%.

7-2) Step h': Synthesis of 3-O-[2,3,4-tri-O-(t-butyldimethylsilyl)-6-deoxy-6-acetylthio-α-D-glucopyranosyl]-1,2-di-O-oleoyl-glycerol (IX'-1) and 3-O-[2,3,4-tri-O-(t-butyldimethylsilyl)-6-deoxy-6-acetylthio-α-D-glucopyranosyl]-1-O-oleoyl-glycerol (IX'-2)

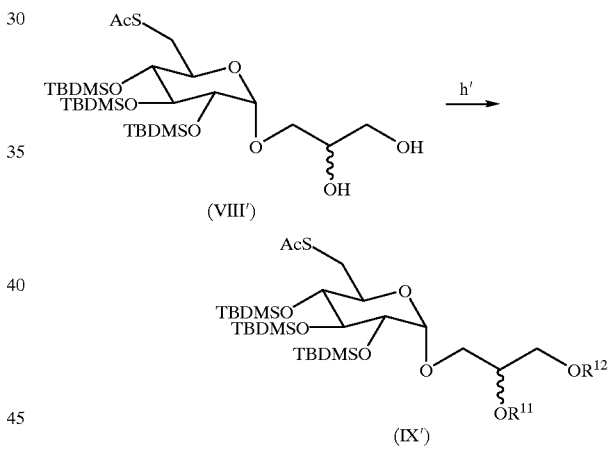

where IX'-1: $R^{11}$=$R^{12}$=oleoyl; IX'-2: $R^{11}$=H, $R^{12}$=oleoyl.

Into 20 mL of anhydrous dichloromethane, 1.37 g (2.09 mmol) of 3-O-[2,3,4-tri-O-(t-butyldimethylsilyl)-6-deoxy-6-acetylthio-α-D-glucopyranosyl)-glycerol (VIII') were dissolved and then 1.46 g of EDCl, 538 mg of DMAP, and 660 mg of oleic acid were added. The solution was reacted at room temperature for 16 hours while stirring. Thereafter, the reaction was quenched by adding 200 mL of dichloromethane, and the reaction mixture was washed with saturated aqueous sodium chloride (2×100 mL), dried over anhydrous sodium sulfate, filtered, concentrated in vacuo, and purified by silica gel flash chromatography (hexane:ethyl acetate=20:1→10:1→7:1) to give 772 mg (652 μmol) of the diester and 895 mg (974 μmol) of the monoester, with yield (total of both the esters) of 78.0%.

7-3-1) Step i'-1: Synthesis of 3-O-[2,3,4-tri-O-(t-butyldimethylsilyl)-6-deoxy-6-sulfo-α-D-glucopyranosyl]-1,2-di-O-oleoyl-glycerol sodium salt (X'-1)

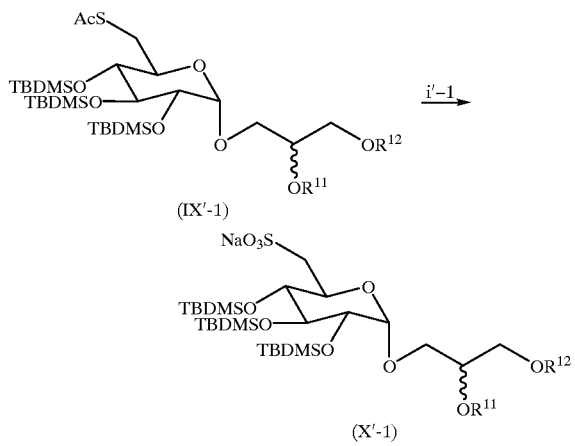

where $R^{11}=R^{12}$=oleoyl.

Into 28 mL of glacial acetic acid, 566 mg (478 μmol) of 3-O-[2,3,4-tri-O-(t-butyldimethylsilyl)-6-deoxy-6-acetylthio-α-D-glucopyranosyl]-1,2-di-O-oleoyl-glycerol (IX'-1) were dissolved and then 3.2 g of potassium acetate and 980 mg of OXONE were added. The solution was reacted at room temperature for 6 hours while stirring. Thereafter, the reaction was quenched by adding 15 mL of cold distilled water, and the reaction mixture was extracted with ethyl acetate (5×20 mL). The organic layers were combined, neutralized with saturated sodium hydrogencarbonate (5×70 mL), washed with saturated aqueous sodium chloride (2×60 mL), dried over anhydrous sodium sulfate, filtered, concentrated in vacuo, and purified by silica gel flash chromatography (dichloromethane:methanol= 50:1→10:1) to give 152 mg (126 μmol) of the title compound with yield of 26.4%.

7-3-2) Step i'-2: Synthesis of 3-O-[2,3,4-tri-O-(t-butyldimethylsilyl)-6-deoxy-6-sulfo-α-D-glucopyranosyl]-1-O-oleoyl-glycerol sodium salt (X'-2)

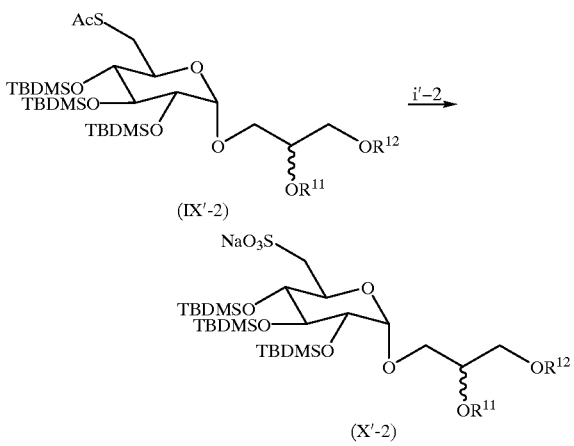

where $R^{11}$=H, $R^{12}$=oleoyl.

Into 3.5 mL of glacial acetic acid, 21.4 mg (23.2 μmol) of 3-O-[2,3,4-tri-O-(t-butyldimethylsilyl)-6-deoxy-6-acetylthio-α-D-glucopyranosyl]-1-O-oleoyl-glycerol (IX'-2) were dissolved and then 500 mg of potassium acetate and 35.4 mg of OXONE were added. The solution was reacted at room temperature for 6 hours while stirring. Thereafter, the reaction was quenched by adding 15 mL of cold distilled water, and the reaction mixture was extracted with ethyl acetate (5×20 mL). The organic layers were combined, neutralized with saturated sodium hydrogencarbonate (5×70 mL), washed with saturated aqueous sodium chloride (2×60 mL), dried over anhydrous sodium sulfate, filtered, concentrated in vacuo, and purified by silica gel flash chromatography (dichloromethane:methanol=50:1→20:1) to give 7.70 mg (8.13 μmol) of the title compound with yield of 34.9%.

7-4-1) Step j'-1: Synthesis of 3-O-(6-deoxy-6-sulfo-α-D-glucopyranosyl)-1,2-di-O-oleoyl-glycerol sodium salt (XI'-1)

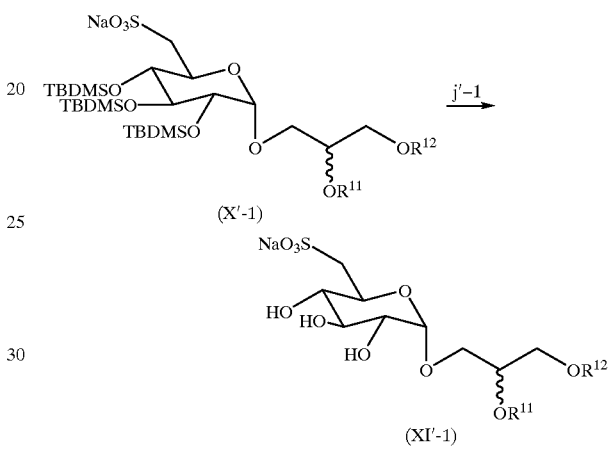

where $R^{11}$, $R^{12}$=oleoyl.

Into 5 mL of a mixture of acetic acid, tetrahydrofuran, trifluoroacetic acid and water (3:1:0.4:1), 214 mg (176 μmol) of a sodium salt (X'-1) of 3-O-[2,3,4-tri-O-(t-butyldimethylsilyl)-6-deoxy-6-sulfo-α-D-glucopyranosyl]-1,2-di-O-oleoyl-glycerol were dissolved. The solution was reacted at room temperature for 16 hours while stirring, and the reaction mixture was extracted with ethyl acetate (3×10 mL). The organic layers were combined, washed with saturated sodium chloride solution (2×20 mL), dried over anhydrous sodium sulfate, filtered, concentrated in vacuo, and purified by silica gel flash chromatography (dichloromethane:methanol= 10:1→dichloromethane:methanol:water=65:25:4) to give 84.1 mg (99.1 μmol) of the title compound with yield of 56.3%.

7-4-2) Step j'-2: Synthesis of 3-O-(6-deoxy-6-sulfo-α-D-glucopyranosyl)-1-O-oleoyl-glycerol sodium salt (XI'-2)

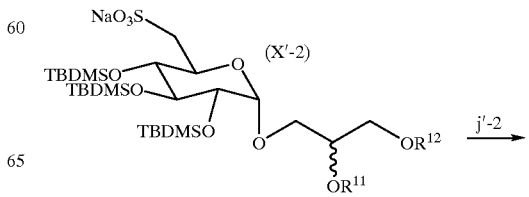

-continued

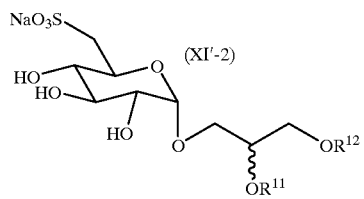

where $R^{11}$=H, $R^{12}$=oleoyl.

Into 7 mL of a mixture of acetic acid, tetrahydrofuran, trifluoroacetic acid and water (3:1:0.4:1), 358 mg (378 μmol) of a sodium salt of 3-O-[2,3,4-tri-O-(t-butyldimethylsilyl)-6-deoxy-6-sulfo-α-D-glucopyranosyl]-1-O-oleoyl-glycerol (X'-2) were dissolved. The solution was reacted at room temperature for 16 hours while stirring, and the reaction mixture was extracted with ethyl acetate (3×10 mL). The organic layers were combined, washed with saturated sodium chloride solution (2×20 mL), dried over anhydrous sodium sulfate, filtered, concentrated in vacuo, and purified by silica gel flash chromatography (dichloromethane:methanol=10:1→dichloromethane:methanol:water=65:25:4) to give 138 mg (237 μmol) of the title compound with yield of 62.7%.

<Example 8: Synthesis of a 3-O-(6-deoxy-6-sulfo-β-D-glucopyranosyl)-1-O-palmitoyl-glycerol sodium salt>

Using 2,3,4-tri-O-benzyl-1-O-(2-propenyl)-6-O-(4-tolylsulfonyl)-β-D-glucose, which has been obtained in the step g in Example 1, the same manners as in the step f in Example 4, as well as the steps g, h, i-2 and j-2 in Example 6 were carried out to yield 1.52 mg (3.10 μmol) of the title compound as a white crystal, with yield of 22.5%. Melting point: 80–82° C.; $[α]_D$=+0.4° ($CHCl_3$).

Figure 5:
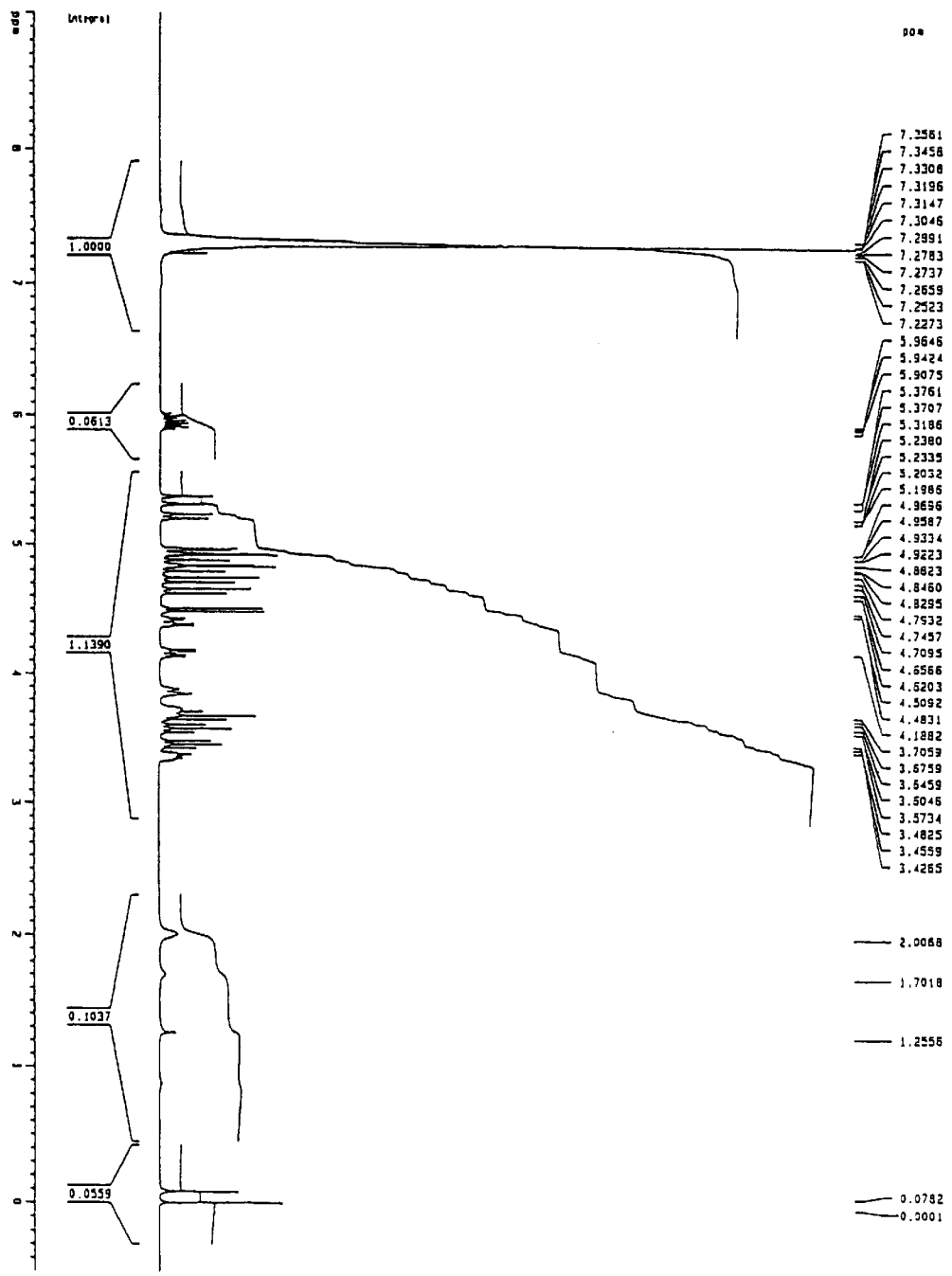
FIG. 5 is a $^1$H NMR chart of 2,3,4-tri-O-benzyl-1-O-(2-propenyl)-β-D-glucose of the formula (VII), which was produced in Example 1 which will be described later.
Figure 6:
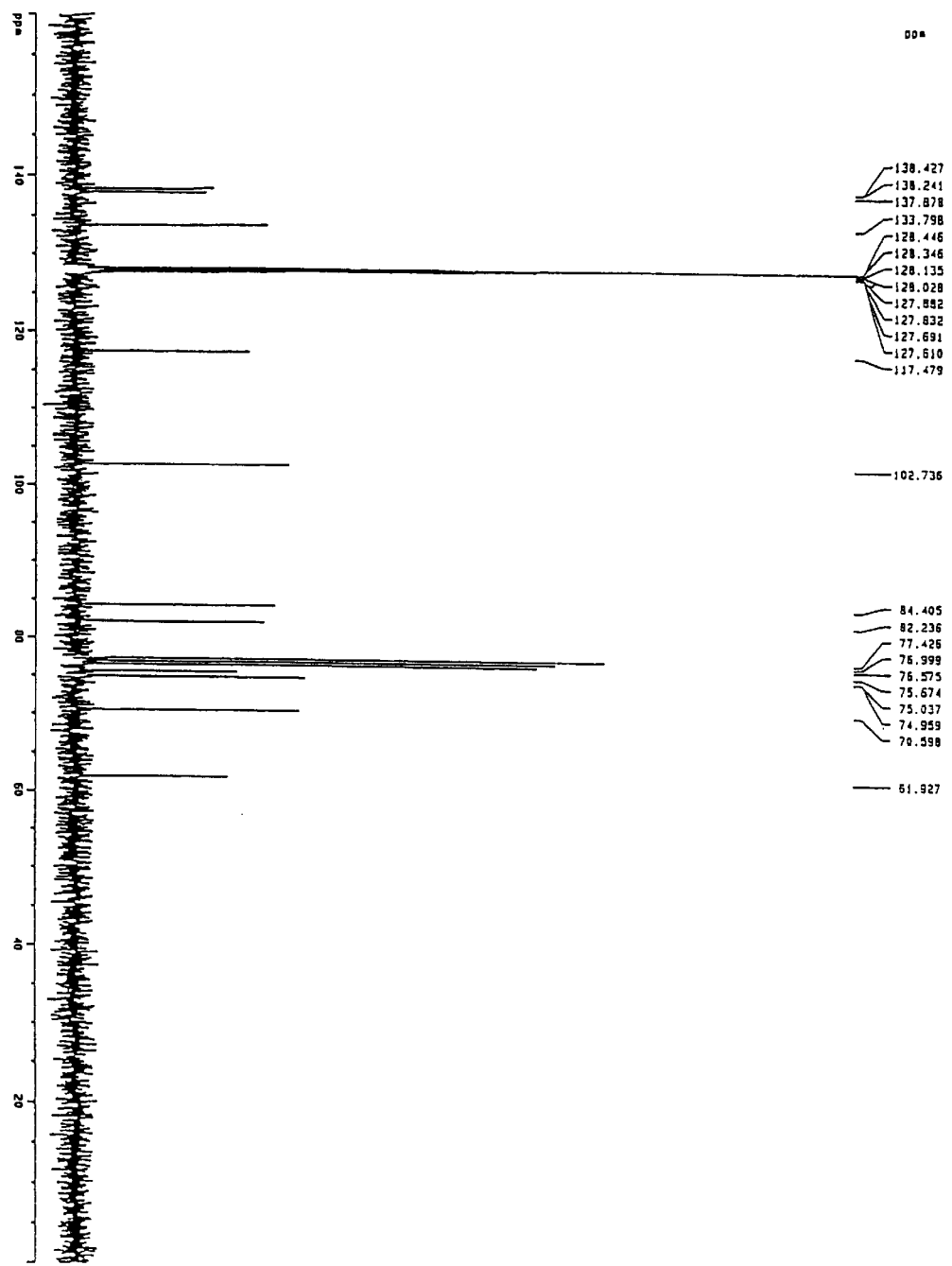
FIG. 6 is a $^{13}$C NMR chart of 2,3,4-tri-O-benzyl-1-O-(2-propenyl)-β-D-glucose of the formula (VII), which was produced in Example 1 which will be described later.

FIG. 5 is a chart of $^1H$ NMR (75 MHz, $CDCl_3$) in which tetramethylsilane was used as an internal standard substance, while FIG. 6 is a chart of $^{13}C$ NMR (300 MHz, $CDCl_3$) of the compound obtained.

<Assay 1>

Mixed lymphocytes reaction

Lymphocytes serving as stimulator cells and responder cells were prepared from blood taken from individual healthy persons.

The responder cells were further separated from the lymphocyte cells to give T lymphocytes alone.

No treatment was applied to the responder cells. $10^6$/mL of the stimulator cells were treated with 10 μg/mL of mitomycin C to stop the cell growth. Thereafter, the stimulator cells were washed with PBS (phosphate buffer saline) 4 times.

Subsequently, the responder cells were inoculated at a rate of $10^5$ cells per well and then test substances (compounds SQAG 3, SQAG 5, SQAG 7, and SQAG 9 listed in Table 6 below) were added to a predetermined concentration. The reaction mixture was cultured at 37° C. for one hour. Thereafter, the stimulator cells were added at a rate of $10^5$ cells per well. The mixture was cultured in a $CO_2$ incubator at 37° C. for 4 days. After the incubation, the proliferation ability of the responder cells was quantified as follows. First, [$^3H$]-thymidine was added to the responder cells and incorporated into the nucleus of the cells by culturing the cells for 12 hours. Then, the amount of [$^3H$]-thymidine uptake into the cells was determined by a scintillation counter.

TABLE 6

(1-1)

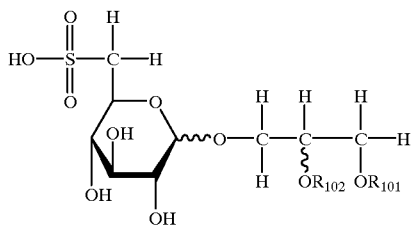

| Compound | $R_{101}$— | $R_{102}$— | Bonding between glucose and glyceride |
|---|---|---|---|
| SQAG 3 | $CH_3(CH_2)_{14}CO$— | $CH_3(CH_2)_{14}CO$— | α |
| SQAG 5 | $CH_3(CH_2)_{16}CO$— | $CH_3(CH_2)_{16}CO$— | α |
| SQAG 7 | $CH_3(CH_2)_{14}CO$— | $CH_3(CH_2)_{14}CO$— | β |
| SQAG 9 | $CH_3(CH_2)_{16}CO$— | $CH_3(CH_2)_{16}CO$— | β |

The results are shown in FIGS. 1–4.

FIGS. 1–4 show the amounts of [$^3H$]-thymidine uptake when SQAG 3, SQAG 5, SQAG 7, and SQAG 9 are added. The lower the amount of [$^3H$]-thymidine uptake, the higher the immunosuppressive activity. In each of the FIGS. 1–4, the vertical axis indicates the intensity of radioactivity and the horizontal axis indicates the concentration of the test substance.

As is apparent from FIGS. 1–4, all test substances have significant immunosuppressive activities. In particular, SQAG 9 has a considerably higher immunosuppressive activity than other compounds.

<Assay 2>

Rejection test in skin graft

ACI rats and LEW rats were prepared and subjected to inhalation anesthesia of ether. After shaving the dorsum of each ACI rat, posterior lateral skin (1×1 cm) was removed to form a skin-flayed wound, and then a hemostatic treatment was performed. On the other hand, a piece of skin (1×1 cm) was obtained from the tail of each LEW rat. The donor skin was applied to the skin-flayed wound of each ACI rat and sutured with 5-0 nylon sutures. Then, gauze was applied to the surgically operated portion and a corset with a rubber bandage was further attached thereon to protect it. Such a skin transplantation operation was applied to all ten ACI rats in the same manner. Of the ten ACT rats, five rats were selected at random and classified as a control group, and the remaining five rats were classified as a test group to which test substances are to be administered. To the control group, 10 mL of physiological saline was intraperitoneally injected daily for five days after the surgery. To the test group, 10 mL solution of SQAG 9 dissolved in physiological saline at a concentration of 1 mg/mL was intraperitoneally injected daily for five days after the surgery in the same manner as in the control group.

On the seventh day after the operation, a graft was taken to prepare a tissue specimen. Subsequently, H-E staining was performed in accordance with the method of Fujita et al.

<Assay 3>

An assay on inhibitory effect against a DNA polymerase α was carried out in the following manner.

0.05 U of a DNA polymerase α isolated from the bovine thymus and purified with an antibody column was mixed with each of compounds SQAG 1 to SQAG 14 listed in Table 1 above, each of which was dissolved in DMSO. Each mixture was added with a buffer of an inorganic salt necessary for the enzymatic reaction, [$^3$H]-labeled dTTP, and a compound for reaction containing a template DNA chain, and was incubated at 37° C. for 60 minutes.

After the enzymatic reaction was stopped, the resultant product was fixed on a dedicated filter to make measurement by a liquid scintillation counter. The amount of enzymatically synthesized dTTP was calculated as a radiation dose (cpm) of [$^3$H].

The results are shown as $IC_{50}$ in Table 7 below.

TABLE 7

Inhibition Activity against DNA Polymerase α

| Compound | SQAG 1 | SQAG 2 | SQAG 3 | SQAG 4 | SQAG 5 | SQAG 6 | SQAG 7 | SQAG 8 | SQAG 9 | SQAG 10 | SQAG 11 | SQAG 12 | SQAG 13 | SQAG 14 |
|---|---|---|---|---|---|---|---|---|---|---|---|---|---|---|
| $IC_{50}$ (μg/mL) | 0.80 | 4.50 | 0.40 | 3.50 | 0.30 | 2.40 | 0.30 | 4.00 | 0.30 | 3.00 | 1.20 | 1.00 | 1.00 | 1.00 |

(T. Fujita, S. Takahashi, A. Yagihashi, K. Jimbow, N. Sato, Transplantation, vol. 64, 922–925, 1997). The results were histologically examined.

As a result of histological observation, it was confirmed that the epidermal layer was removed from the dermis in all five rats of the control group, and that necrosis of the epidermis had occurred. In contrast, necrosis of the epidermal layer was observed in three out of five rats in the SQAG 9 administered group. However, in the remaining two rats, it was observed that some parts of the epidermis successfully adhered to the derims even though other parts of the epidermal layer were partly removed from the dermis.

The present inventors consider that the skin graft rejection test is the most stringent method of evaluation for an immunosuppressive activity. It is considered that rejection occurred most severely when transplantation was made between the ACI series rats and the LEW series rats, as used in this assay. However, under such stringent conditions, the activity for suppressing the rejection was observed in two out of five rats in this assay. This fact demonstrates that SQAGs of the present invention are highly effective as an immumosuppressive agent.

In addition, none of the rats administered with SQAGs died from acute toxicity during the test period. Neither weight reduction nor malphysical conditions were visually observed. No abnormality was observed with respect to major organs in general pathological tests. It is therefore demonstrated that the immunosuppressive agents of the present invention are extremely low in toxicity.

Of the commercially available immunosuppressive agents, a few (e.g., FK506) are known as effective in suppressing rejection in skin graft tests. However, highly effective immunosuppressive agents low in toxicity have not yet been reported.

In the following assays, each of the sulfoquinovosylacylglycerol derivatives used was a mixture of S- and R-configurations.

As is clear from Table 7, the compounds subjected to the assay exhibited different inhibitory activity levels, i.e., from low levels to high levels, against the DNA polymerase α.

Colon cancer cells and gastric cancer cells used in the following two assays are merely examples of cancer cells for which the anticancer agent of the present invention is effective. Thus, these assays are not intended to limit cancer cells for which the anticancer agent of the present invention is effective.

Examples of other cancer cells include those of esophageal cancer, gastric cancer, colon cancer, including those at colon and recta, thyroid cancer, bladder cancer, kidney cancer, prostatic cancer, malignant lymphoma, brain tumor, lung cancer, laryngeal cancer, pharyngeal cancer, hepatic cancer, gallbladder cancer, bile duct cancer, pancreas cancer, breast cancer, uterine cancer, ovarian cancer, vaginal cancer, leukemia, childhood cancer, skin cancer, osteosarcoma, tongue cancer, cancer of small intestine, penile cancer, urethral cancer, ureteral cancer, testicular cancer, thymoma and myeroma.

<Assay 4>

An assay on anticancer activity against cultured colon cancer cells was carried out in the following manner.

Colon cancer cells DLD-1 were maintained and subcultured in RPMI 1640 medium (containing 10% calf serum). Each of compounds SQAG 1, SQAG 2, SQAG 4, SQAG 6, SQAG 8, SQAG 11, SQAG 12, SQAG 13 and SQAG 14 shown in Table 1 was suspended and diluted in the medium, and then was cultivated in a 96-well plate together with the cancer cells at 3×10$^3$ cells/well. After the culture has been incubated for 48 hours, the MTT assay (Mosmann, T: Journal of immunological Method, 65, 55–63 (1983)) was carried out to compare viability rates.

The results are shown as $IC_{50}$ in Table 8.

TABLE 8

Anti-Cancer Activity against Colon Cancer Cells

| Compound | SQAG 1 | SQAG 2 | SQAG 4 | SQAG 6 | SQAG 8 | SQAG 11 | SQAG 12 | SQAG 13 | SQAG 14 |
|---|---|---|---|---|---|---|---|---|---|
| $IC_{50}$ (μg/mL) | 38 | 40 | 31 | 30 | 42 | 28 | 20 | 20 | 18 |

As is clear from Table 8, all of the compounds tested have a significant anticancer activity against the colon cancer cells.

It can be considered that each of the compounds independently has an anticancer activity equal to or more than that of a mixture of the sulfoquinovosylacylglycerol derivatives disclosed by Sahara et al. (British journal of cancer, 75 (3), 324–332 (1997)) described previously.

<Assay 5>

An assay on anticancer activity against cultured gastric cancer cells was carried out in the same manner as in the assay 4 except that gastric cancer cells NUGC-3 were used instead of the colon cancer cells DLD-1.

The results are shown as $IC_{50}$ in Table 9.

TABLE 9

Anticancer Activity against Gastric Cancer Cells

| Compound | SQAG 1 | SQAG 2 | SQAG 4 | SQAG 6 | SQAG 8 | SQAG 11 | SQAG 12 | SQAG 13 | SQAG 14 |
|---|---|---|---|---|---|---|---|---|---|
| $IC_{50}$ (μg/mL) | 32 | 40 | 40 | 37.5 | 50 | 24 | 23 | 20 | 20 |

As is clear from Table 9, all of the compounds tested have a significant anticancer activity against the gastric cancer cells.

It can be considered that each of the compounds tested singly has an anticancer activity equal to or more than that of a mixture of the sulfoquinovosylacylglycerol derivatives disclosed by Sahara et al. (British journal of cancer, 75 (3), 324–332 (1997)).

The sulfoquinovosylacylglycerol derivatives represented by Formula (1) which are used as effective ingredients in the anticancer agent of the present invention have an inhibitory effect against DNA polymerase α (see the Assay 1). It is known that there are DNA polymerases β, γ, δ and ε, in addition to the DNA polymerase α. Among these DNA polymerases, the δ and ε are biochemical analogues to the α. The biochemical analogues mean that they are common in enzymatic functions as follows. (i) Existence or non-existence of sensitivity to a specific compound: For example, these three types of DNA polymerases have sensitivity to N-ethylmaleimide and butylphenyl-dGTP, but do not have sensitivity to dideoxy TTP (ddTTP). (ii) Fidelity: They have high accuracy in DNA synthesis with respect to a template DNA. (iii) Reaction site: These three types of DNA polymerases are directly involved in DNA replication which is co-operated with cell division.

The DNA polymerase α (including δ and ε as biochemical analogues) is generally considered to control DNA synthesis correspondingly to the cell cycle. The inventors consider that the compounds represented by Formula (1) according to the present invention have inhibitory activity against not only the DNA polymerase α but also the DNA polymerases δ and ε.

Additional advantages and modifications will readily occur to those skilled in the art. Therefore, the present invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A method for immunosuppression in a subject comprising administering to the subject in need thereof, an immunosuppressively effective amount of at least one sulfoquinovosylacylglycerol compound represented by formula (1-1):

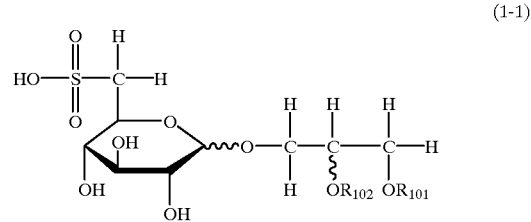

(1-1)

wherein $R_{101}$ represents an acyl residue of a higher fatty acid represented by R—C(=O)—, wherein R represents an alkyl or alkenyl group each having 13–25 carbon atoms, and $R_{102}$ represents a hydrogen atom or an acyl residue of a higher fatty acid represented by R'—C(=O)—, wherein R' represents an alkyl or alkenyl group each having 13—25 carbon atoms; or a pharmaceutically acceptable salt thereof.

2. The method according to claim 1, wherein the bonding between sulfoquinovose and glycerol in the formula (1-1) is in the α-anomeric configuration.

3. The method according to claim 2, wherein $R_{102}$ of the formula (1-1) represents an acyl residue of a higher fatty acid represented by R'—C(=O)—, wherein R' represents an alkyl or alkenyl group having 13–25 carbon atoms.

4. The method according to claim 3, wherein the acyl residue of $R_{101}$ and $R_{102}$ is independently represented by formula:

wherein n is an integer of 12–24.

5. The method according to claim 2, wherein $R_{102}$ of the formula (1-1) represents a hydrogen atom.

6. The method according to claim 5, wherein the acyl residue of $R_{101}$ is represented by formula:

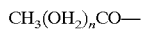

wherein n is an integer of 12–24.

7. The method according to claim 2, wherein R of $R_{101}$ represents an alkenyl group having 13–25 carbon atoms, and $R_{102}$ represents a hydrogen atom or an acyl residue of an unsaturated higher fatty acid represented by R'C(=O)—, wherein R' represents an alkenyl group having 13–25 carbon atoms.

8. A sulfoquinovosylacylglycerol compound represented by formula (1-2):

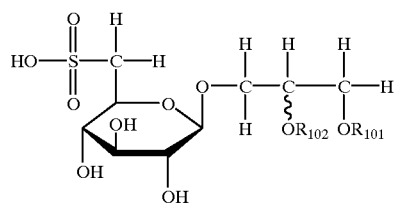

wherein $R_{101}$ represents an acyl residue of a higher fatty acid, and $R_{102}$ represents a hydrogen atom or an acyl residue of a higher fatty acid, or a pharmaceutically acceptable salt thereof.

9. The sulfoquinovosylacylglycerol compound or a pharmaceutically acceptable salt thereof according to claim 8, wherein $R_{101}$ and $R_{102}$ independently represent an acyl residue of a higher fatty acid represented by R—C(=O)—, wherein R represents an alkyl or alkenyl group each having 13–25 carbon atoms.

10. The sulfoquinovosylacylglycerol compound or a pharmaceutically acceptable salt thereof according to claim 9, wherein the acyl residue is represented by formula:

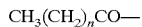

wherein n is an integer of 12–24.

11. The sulfoquinovosylacylglycerol compound or a pharmaceutically acceptable salt thereof according to claim 8, wherein $R_{101}$ represents an acyl residue of a higher fatty acid represented by R—C(=O)—, wherein R represents an alkyl or alkenyl group each having 13–25 carbon atoms, and $R_{102}$ represents a hydrogen atom.

12. The sulfoquinovosylacylglycerol compound or a pharmaceutically acceptable salt thereof according to claim 11, wherein the acyl residue of $R_{101}$ is represented by formula:

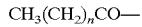

wherein n is an integer of 12–24.

13. The sulfoquinovosylacylglycerol compound or a pharmaceutically acceptable salt thereof according to claim 8, wherein $R_{101}$ represents an acyl residue of an unsaturated higher fatty acid represented by R—C(=O)—, wherein R represents an alkenyl group having 13–25 carbon atoms, and $R_{102}$ represents a hydrogen atom or an acyl residue of an unsaturated higher fatty acid represented by R'—C(=O)—, wherein R' represents an alkenyl group having 13–25 carbon atoms.

14. A pharmaceutical composition comprising a pharmaceutically effective amount of the sulfoquinovosylacylglycerol compound represented by the following formula (1-2) or a pharmaceutically acceptable salt thereof:

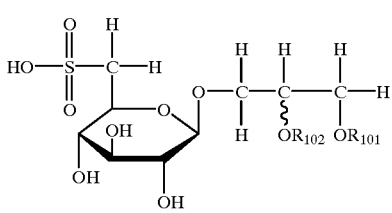

wherein $R_{101}$ represents an acyl residue of a higher fatty acid represented by R—C(=O)—, wherein R represents an alkyl or alkenyl group each having 13–25 carbon atoms, and $R_{102}$ represents a hydrogen atom or an acyl residue of a higher fatty acid represented by R'—C(=O)—, wherein R' represents an alkyl or alkenyl group having 13–25 carbon atoms; and a pharmaceutically acceptable excipient.

15. The pharmaceutical composition according to claim 14, wherein $R_{102}$ of the formula (1-2) represents an acyl residue of a higher fatty acid represented by R'—C(=O)—, wherein R' represents an alkyl or alkenyl group each having 13–25 carbon atoms.

16. The pharmaceutical composition according to claim 15, wherein the acyl residue of $R_{101}$ and $R_{102}$ is independently represented by formula:

wherein n is an integer of 12–24.

17. The pharmaceutical composition according to claim 14, wherein $R_{102}$ of the formula (1-2) represents a hydrogen atom.

18. The pharmaceutical composition according to claim 17, wherein the acyl residue of $R_{101}$ is represented by formula:

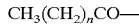

wherein n is an integer of 12–24.

19. The pharmaceutical composition according to claim 14, wherein R of $R_{101}$ represents an alkenyl group having 13–25 carbon atoms, and $R_{102}$ of the formula (1-2) represents a hydrogen atom or an acyl residue of an unsaturated higher fatty acid represented by R'—C(=O)—, wherein R' represents an alkenyl group having 13–25 carbon atoms.

20. The sulfoquinovosylacylglycerol compound or a pharmaceutically acceptable salt thereof according to claim 8, wherein $R_{101}$ represents an acyl residue of a higher fatty acid represented by R—C(=O)—, wherein R represents an alkyl or alkenyl group having 13 to 25 carbon atoms, and $R_{102}$ represents a hydrogen atom or an acyl residue of a higher fatty acid represented by R'—C(=O)—, wherein R' represents an alkyl or alkenyl group each having 13 to 25 carbon atoms.

21. The method according to claim 4, wherein n is 12, 14 or 16.

22. The method according to claim 6, wherein n is 12, 14, 16, 18, 20, 22 or 24.

23. The method according to claim 7, wherein $R_{101}$ represents an oleoyl group, and $R_{102}$ represents a hydrogen atom or an oleoyl group.

24. The sulfoquinovosylacylglycerol compound or a pharmaceutically acceptable salt thereof according to claim 10, wherein n is 12, 14, 16, 18 or 20.

25. The sulfoquinovosylacylglycerol compound or a pharmaceutically acceptable salt thereof according to claim 10, wherein n is 14 or 16.

26. The sulfoquinovosylacylglycerol compound or a pharmaceutically acceptable salt thereof according to claim 12, wherein n is 14 or 16.

27. The pharmaceutical composition according to claim 16, wherein n is 12, 14, 16, 18 or 20.

28. The pharmaceutical composition according to claim 16, wherein n is 14 or 16.

29. The pharmaceutical composition according to claim 18, wherein n is 14 or 16.

* * * * *

UNITED STATES PATENT AND TRADEMARK OFFICE
CERTIFICATE OF CORRECTION

PATENT NO. : 6,518,410 B2  Page 1 of 1
DATED : February 11, 2003
INVENTOR(S) : Takayuki Yamazaki et al.

It is certified that error appears in the above-identified patent and that said Letters Patent is hereby corrected as shown below:

<u>Title page,</u>
Item [63], Related U.S. Application Data, replace "abandoned" with
-- Pat. No. 6,518,248 --.

Signed and Sealed this

Tenth Day of February, 2004

JON W. DUDAS
*Acting Director of the United States Patent and Trademark Office*

UNITED STATES PATENT AND TRADEMARK OFFICE
CERTIFICATE OF CORRECTION

PATENT NO. : 6,518,410 B2
DATED : February 11, 2003
INVENTOR(S) : Takayuki Yamazaki et al.

It is certified that error appears in the above-identified patent and that said Letters Patent is hereby corrected as shown below:

<u>Title page,</u>
Item [56], References Cited, OTHER PUBLICATIONS, "Peer et al.," reference,
"+-L-Fucosidase" should read -- α-L-Fucosidase --.
"H. Sahra et al.," reference, "Sahra" should read -- Sahara --
"Dan M. Gordon et al.," reference, "Dan" should read -- Dana --.

Signed and Sealed this

Tenth Day of May, 2005

JON W. DUDAS
*Director of the United States Patent and Trademark Office*